(12) United States Patent
Chaves et al.

(10) Patent No.: US 7,718,819 B2
(45) Date of Patent: *May 18, 2010

(54) PROCESS FOR MAKING ORGANOFUNCTIONAL SILANES AND MIXTURES THEREOF

(75) Inventors: Antonio Chaves, Chappaqua, NY (US); Eric R. Pohl, Mount Kisco, NY (US); Linda Vecere, Fishkill, NY (US); Lesley Hwang, Chappaqua, NY (US)

(73) Assignee: Momentive Performance Materials Inc., Albany, NY (US)

( * ) Notice: Subject to any disclaimer, the term of this patent is extended or adjusted under 35 U.S.C. 154(b) by 1103 days.

This patent is subject to a terminal disclaimer.

(21) Appl. No.: 11/358,818

(22) Filed: Feb. 21, 2006

(65) Prior Publication Data

US 2007/0197813 A1   Aug. 23, 2007

(51) Int. Cl.
C07F 7/04   (2006.01)
(52) U.S. Cl. ...................... 556/427; 556/429
(58) Field of Classification Search ................. 556/427, 556/429
See application file for complete search history.

(56) References Cited

U.S. PATENT DOCUMENTS

| | | | |
|---|---|---|---|
| 2,731,485 A | 1/1956 | Wagner et al. |
| 2,811,542 A | 10/1957 | Speier et al. |
| 2,967,171 A | 1/1961 | Barnes et al. |
| 3,065,254 A | 11/1962 | Silva |
| 3,069,451 A | 12/1962 | Fritz |
| 3,445,496 A | 5/1969 | Ryan |
| 3,661,954 A | 5/1972 | Legrow |
| 3,692,812 A | 9/1972 | Berger |
| 3,798,196 A | 3/1974 | Rocktaschel |
| 3,846,463 A | 11/1974 | Nagai et al. |
| 3,856,843 A | 12/1974 | Nagai et al. |
| 3,869,340 A | 3/1975 | Kotzsch |
| 3,922,436 A | 11/1975 | Bell et al. |
| 3,946,059 A | 3/1976 | Janssen et al. |
| 3,956,353 A | 5/1976 | Plueddemann |
| 3,971,883 A | 7/1976 | Meeks et al. |
| 4,026,827 A | 5/1977 | Steffen |
| 4,044,037 A | 8/1977 | Mui et al. |
| 4,060,539 A | 11/1977 | Seiler et al. |
| 4,152,347 A | 5/1979 | Pletka et al. |
| 4,332,654 A | 6/1982 | Yates |
| 4,574,133 A | 3/1986 | Umpleby |
| 4,595,740 A | 6/1986 | Panster |
| 4,820,751 A | 4/1989 | Takeshita |
| 5,116,886 A | 5/1992 | Wolff et al. |
| 5,326,895 A | 7/1994 | Kubota et al. |
| 5,663,226 A | 9/1997 | Scholl |
| 5,674,932 A | 10/1997 | Agostini |
| 5,767,216 A | 6/1998 | Frances et al. |
| 5,981,674 A | 11/1999 | Schombourg et al. |
| 6,005,027 A | 12/1999 | Guillet et al. |
| 6,068,125 A | 8/2000 | Cruse |
| 6,127,468 A | 10/2000 | Cruse |
| 6,172,251 B1 | 1/2001 | Parker |
| 6,204,339 B1 | 3/2001 | Waldman |
| 6,331,605 B1 | 12/2001 | Lunginsland et al. |
| 6,359,046 B1 | 3/2002 | Cruse |
| 6,414,061 B1 | 7/2002 | Cruse |
| 6,528,673 B2 | 3/2003 | Cruse |
| 6,548,594 B2 | 4/2003 | Luginsland |
| 6,608,125 B2 | 8/2003 | Cruse |
| 6,635,700 B2 | 10/2003 | Cruse et al. |
| 6,683,135 B2 | 1/2004 | Cruse |
| 6,753,438 B2 | 6/2004 | Taylor |
| 6,777,569 B1 | 8/2004 | Westmeyer |
| 6,849,754 B2 | 2/2005 | Deschler et al. |
| 7,019,174 B2 | 3/2006 | Nakamura et al. |
| 7,064,173 B2 | 6/2006 | Rubinsztajn |
| 7,074,876 B2 | 7/2006 | Cruse |
| 7,078,551 B2 | 7/2006 | Cruse |
| 7,081,500 B2 | 7/2006 | Cruse |
| 7,122,590 B2 | 10/2006 | Cruse |
| 7,169,872 B2 | 1/2007 | Cruse |
| 7,241,851 B2 | 7/2007 | Cella |
| 7,301,042 B2 | 11/2007 | Cruse |
| 7,326,753 B2 | 2/2008 | Weller |
| 2001/0009966 A1 | 7/2001 | Wunsch |

(Continued)

FOREIGN PATENT DOCUMENTS

AU   730753   7/1997

(Continued)

OTHER PUBLICATIONS

U.S. Appl. No. 10/128,804, filed Aug. 2005, Cruse.
U.S. Appl. No. 11/398,125, filed Apr. 2006, Cruse.
U.S. Appl. No. 11/398,132, filed Apr. 2006, Cruse.
Joshi, et al.; "Low VOC Silanes for Silica Tires" Spring Technical Meeting—American Chemical Society, Rubber Division; ISSN 1547-1977, May 2005, XP009072692.
Bonsignore P.V. et al., (1960) Apolyalkylene disulfides and polysulfides containing silcon@, *Journal of Organic Chemstry* 25 pp. 237-240.

(Continued)

*Primary Examiner*—Porfirio Nazario Gonzalez
(74) *Attorney, Agent, or Firm*—Dominick G. Vicari; Joseph S. Ostroff

(57) ABSTRACT

A process is provided for preparing organofunctional silanes, inclusive of dimers and oligomers, in which individual silanes possess both free and blocked mercaptan functionality or particular mixtures of the organofunctional silanes possess both free and blocked mercaptan functionality. The organofunctional silanes and silane mixtures are useful, inter alia, as coupling agents for elastomeric compositions, e.g., rubber formulations employed in the manufacture of tires, where they exhibit a desirable balance of low scorch and good performance properties.

38 Claims, No Drawings

U.S. PATENT DOCUMENTS

| | | |
|---|---|---|
| 2002/0016487 A1 | 2/2002 | Kayser et al. |
| 2003/0055139 A1 | 3/2003 | Cruse |
| 2003/0130388 A1 | 7/2003 | Luginsland et al. |
| 2003/0139287 A1 | 7/2003 | Deforth |
| 2003/0195370 A1 | 10/2003 | Taylor |
| 2003/0199619 A1 | 10/2003 | Cruse et al. |
| 2004/0014840 A1 | 1/2004 | Hong et al. |
| 2004/0127668 A1 | 7/2004 | Rubinsztajn |
| 2005/0009955 A1 | 1/2005 | Cohen et al. |
| 2005/0033001 A1 | 2/2005 | Cella |
| 2005/0245753 A1 | 11/2005 | Cruse |
| 2005/0245754 A1 | 11/2005 | Glatzer |
| 2006/0025506 A1 | 2/2006 | Weller |
| 2006/0036034 A1 | 2/2006 | Chaves |
| 2006/0041063 A1 | 2/2006 | Cruse |
| 2006/0178487 A1 | 8/2006 | Weller |
| 2006/0183831 A1 | 8/2006 | Hsu et al. |
| 2006/0183866 A1 | 8/2006 | Pohl |
| 2006/0217474 A1 | 9/2006 | Cruse et al. |
| 2006/0281841 A1 | 12/2006 | Weller |
| 2007/0083011 A1 | 4/2007 | Pohl |
| 2007/0185279 A1 | 8/2007 | Cruse |
| 2007/0197725 A1 | 8/2007 | Chaves |
| 2007/0197812 A1* | 8/2007 | Chaves et al. ............... 556/427 |
| 2007/0197813 A1 | 8/2007 | Chaves |
| 2007/0228322 A1 | 10/2007 | Chaves |
| 2008/0039561 A1 | 2/2008 | Chaves |
| 2008/0039562 A1 | 2/2008 | Chaves et al. |
| 2008/0039644 A1 | 2/2008 | Chaves |
| 2008/0039645 A1 | 2/2008 | Chaves |

FOREIGN PATENT DOCUMENTS

| | | |
|---|---|---|
| DE | 2050467 | 5/1971 |
| DE | 19957325 A | 5/2001 |
| DE | 10163945 | 12/2001 |
| DE | 10163945 | 5/2003 |
| DE | 10163945 C1 | 5/2003 |
| EP | 0097 516 | 1/1984 |
| EP | 0097516 | 1/1984 |
| EP | 0 211 154 A | 2/1987 |
| EP | 0291871 | 11/1988 |
| EP | 0396 364 | 11/1990 |
| EP | 0631 982 | 1/1995 |
| EP | 0631982 | 1/1995 |
| EP | 784072 | 7/1997 |
| EP | 0784072 A1 | 7/1997 |
| EP | 1002835 A | 5/2000 |
| FR | 2 382 456 | 9/1978 |
| JP | 58176538 | 10/1983 |
| JP | 07258474 | 10/1995 |
| JP | H07258474 | 10/1995 |
| RU | 2 123 016 1 | 12/1998 |
| WO | WO99/09036 | 2/1999 |
| WO | WO 99 09036 A1 | 2/1999 |
| WO | WO99/20682 | 4/1999 |
| WO | WO 02/48256 A2 | 6/2002 |
| WO | WO2003/091314 | 11/2003 |
| WO | WO2004/005395 | 1/2004 |
| WO | WO 2004/005395 | 1/2004 |
| WO | WO 2004/045552 A2 | 6/2004 |
| WO | WO2005/007660 | 1/2005 |
| WO | WO 2005/007660 A1 | 1/2005 |
| WO | WO2005/040272 | 5/2005 |
| WO | WO 2005/040272 A1 | 5/2005 |
| WO | WO 2006/019963 | 2/2006 |
| WO | WO 2006/019963 A1 | 2/2006 |
| WO | WO 2006/023785 | 3/2006 |
| WO | WO 2006/023815 | 3/2006 |
| WO | WO 2006/023815 A2 | 3/2006 |
| WO | WO 2007/098080 | 8/2007 |
| WO | WO 2007/098121 | 8/2007 |
| WO | WO 2007/098121 A2 | 8/2007 |

OTHER PUBLICATIONS

Takiguchi T. et al. (1983) Some Fundamental Investigations Viewed in Industrial Aspects on the Synthesis of Organosilicon Monomers and Polymers with Some Novel Properties and Functions @, *AGKGAA* 43 pp. 75-82.

U.S. Appl. No. 11/358,861, filed Feb. 2006, Chaves et al.

Dvorak, M. et al. (1977) A carbonfunctional organosilicon compounds substituted in the .alpha-position. II. Phosphorus-containing organosilicon compounds substituted in the .alpha.-position. II. Phosphorus-containing organosilicon compounds@. *Chemicky Prumysl*, 27(5), pp. 9-2789.

Andrianov, K.A. et al. (1962) A reaction of replacement of chlorine in .alpha.-chloromethylmethylalkoxysilanes by residues of diethyl or dibutyl dithiophosphoric or diphenyldithiophosphinic acids@., *izvestiya Akademii Nauk SSSR*, pp. 2-3353.

U.S. Appl. No. 10/903,960, filed Jul. 2004, Weller.
U.S. Appl. No. 10/918,828, filed Aug. 2004, Weller.
U.S. Appl. No. 10/922,426, filed Aug. 2004, Cruse et al.
U.S. Appl. No. 11/104,103, filed Apr. 2005, Chaves et al.
U.S. Appl. No. 11/208,367, filed Aug. 2005, Cruse et al.
U.S. Appl. No. 11/358,369, filed Feb. 2006, Chaves et al.
U.S. Appl. No. 11/358,550, filed Feb. 2006, Chaves et al.
U.S. Appl. No. 11/358,818, filed Feb. 2006, Chaves et al.
U.S. Appl. No. 11/505,166, filed Aug. 2006, Chaves et al.
U.S. Appl. No. 11/505,055, filed Aug. 2006, Chaves et al.
U.S. Appl. No. 11/505,178, filed Aug. 2006, Chaves et al.

"The Siloxane Bond, Physical Properties and Chemical Transformations", M.G. Voronkov, V.P. Mileshkevich and Yu. A. Yuzhelevskii, Consultant Bureau, a Division of Plenum Publishing Company, New York (1978), Chapter 5.

Teng, Zhu et al.; "Palladium-induced intramolecular coupling reactions of some alkenyl (2-iodobenzyl)silanes" Helvetica Chimica Acta, 82,(4), pp. 515-521, Coden:HCACAV; ISSN:0018019x, 1999, xp002372297.

Joshi, P.G., "Low Silanes for Silica Tires" Spring Technical Meeting—American Chemical Society, Rubber Division. 16th San Antonio, Texas, USA (Jun. 16, 2005).

Chemical Abstract, vol. 133, No. 164751, Sep. 1, 2000, Columbus, Ohio, U.S. Abstract No. 2000:607472, Katova, S.A.; Osipchik, V.S., Lebedeva, E.D., Vasilets, L.G. :"Crosslinking composition based on high density polyethylene and vinyltris(beta-ethoxyethoxy)silane" XP002387517 Abstract.

Teng, Zhu et al.; "Palladium-induced intramolecular coupling reactions of some alkenyl (2-iodobenzyl)silanes" Helvetica Chimica Acta, 82,(4), 515-521, Coden:HCACAV;ISSN: 0018-019X, 1999, XP002372297.

Parks et al.; "Studies on the Mechanism of B(C6F5)3-Catalyzed Hydrosilation of Carbonyl Functions"; J. Org. Chem. 2000, 65, 3090-3098; Nov. 30, 1999.

Parks et al.; "Tris(pentafluorophenyl)boron-Catalyzed Hydrosilation of Aromatic Aldehydes, Ketones, and Esters"; J. Org. Chem. Soc. 1996, 118, 9440-9441; May 7, 1996.

Dias et al.; "Synthesis and Properties of a Stable, Cationic, Rhodium Lewis-acid Catalyst for Hydrosilation, Mukaiyama Aldol and Cyclopropanation Reactions"; Royal Society of Chemistry 2001, Chem. Commun. 2001, 423-424.

GE Advanced Materials, Silicones, Low VOC Silanes for Silica Tire; Feb. 22, 2005.

* cited by examiner

US 7,718,819 B2

PROCESS FOR MAKING ORGANOFUNCTIONAL SILANES AND MIXTURES THEREOF

FIELD OF THE INVENTION

The present invention relates to a process for making organofunctional silanes and mixtures of organofunctional silanes possessing mercaptan and blocked mercaptan functionalities.

DESCRIPTION OF THE RELATED ART

Glycol derivatives of organosilanes are known in the art. However, these silane derivatives suffer from a tendency to yield bridged structures in favor of cyclic structures exclusively or primarily, leading to high viscosities and gellation, which limits their usefulness in elastomer manufacture.

Polyether-based monol derivatives of sulfur silanes are also known. Their use suffers from the hazards associated with the use of ethers, which have a tendency to spontaneously form peroxides thus presenting a substantial flammability risk, as well as the possibility of interfering with the usefulness of the silanes as coupling agents in elastomers.

Blocked mercaptosilanes, such as thiocarboxylate-functional silanes, are described, e.g., in U.S. Pat. Nos. 6,127,468, 6,414,061 and 6,528,673. A presentation on the subject of blocked mercaptosilanes was also given at the 2002 International Tire Exposition and Conference (ITEC) in Akron, Ohio. The blocked mercaptosilanes of these patents possess hydrolyzable groups which are derived from simple monofunctional alcohols. When employed as coupling agents for rubber compositions used in the manufacture of tires, the thiocarboxalate-functional silanes of U.S. Pat. Nos. 6,127,468, 6,414,061 and 6,528,673 allow tires to be manufactured with fewer steps. However, during the rubber compounding operation, these blocked mercaptosilanes generate volatile organic compound (VOC) emissions.

This concern regarding VOC emissions, which represents a growing environmental problem in the use of silane coupling agents is addressed, by the cyclic diol-derived blocked organofunctional dimeric and oligomeric silanes described in published U.S. Patent Application 2005/0245753 and U.S. patent application Ser. Nos. 11/104,103, filed Apr. 12, 2005, and Ser. No. 11/208,367, filed Aug. 19, 2005. Another approach to the issue of VOC emissions is the use of high boiling monofunctional alcohol-derived silanes as disclosed in U.S. Pat. No. 6,849,754.

In addition to the need to reduce VOC's during the preparation of inorganic filled elastomers, there is also a need to improve the coupling efficiency between the inorganic filler and organic polymer while maintaining processability of the elastomeric compositions. Better coupling improves the performance of cured articles, such as tires, by reducing rolling resistance, heat build-up and wear. U.S. Pat. No. 6,635,700 describes the use of a mixture of free and blocked mercaptosilanes to achieve better coupling. However, these mixtures emit VOC's upon use. The level of mercaptosilane in these mixtures is limited because this additive reduces the scorch time of the uncured filled elastomer. In an attempt to lengthen the scorch time of uncured filled elastomers containing mercaptosilanes, published U.S. Patent Application 2004/0014840 discloses the use of thiuram disulfide accelerators in combination with functionalized organosilane.

SUMMARY OF THE INVENTION

The present invention provides a process for making an organofunctional silane composition possessing mercaptan functionality and blocked mercaptan functionality which comprises:

a) reacting at least one silane reactant possessing mercaptan functionality or blocked mercaptan functionality and further possessing at least one transesterifiable group with at least one polyhydroxy-containing compound under transesterification conditions to provide said organofunctional silane composition; and, optionally, b) treating part or all of the organofunctional silane composition resulting from step (a) to convert part of the blocked mercaptan functionality, if present therein, to mercaptan functionality, or to convert part of the mercaptan functionality, if present therein, to blocked mercaptan functionality, the organofunctional silane composition resulting from step (a) and/or step (b) containing at least one organofunctional silane selected from the group consisting of:

(i) mercaptosilane possessing at least one hydroxyalkoxysilyl group and/or a cyclic dialkoxysilyl group, (ii) blocked mercaptosilane possessing at least one hydroxyalkoxysilyl group and/or a cyclic dialkoxysilyl group, (iii) mercaptosilane dimer in which the silicon atoms of the mercaptosilane units are bonded to each other through a bridging dialkoxy group, each silane unit optionally possessing at least one hydroxyalkoxysilyl group or a cyclic dialkoxysilyl group, (iv) blocked mercaptosilane dimer in which the silicon atoms of the blocked mercaptosilane units are bonded to each other through a bridging dialkoxy group, each silane unit optionally possessing at least one hydroxyalkoxysilyl group or a cyclic dialkoxysilyl group, (v) silane dimer possessing a mercaptosilane unit the silicon atom of which is bonded to the silicon atom of a blocked mercaptosilane unit through a bridging dialkoxy group, each silane unit optionally possessing at least one hydroxyalkoxysilyl group or a cyclic dialkoxysilyl group, (vi) mercaptosilane oligomer in which the silicon atoms of adjacent mercaptosilane units are bonded to each other through a bridging dialkoxy group, the terminal mercaptosilane units possessing at least one hydroxyalkoxysilyl group or a cyclic dialkoxysilyl group, (vii) blocked mercaptosilane oligomer in which the silicon atoms of adjacent blocked mercaptosilane units are bonded to each other through a bridging dialkoxy group, the terminal mercaptosilane units possessing at least one hydroxyalkoxysilyl group or a cyclic dialkoxysilyl group, and (viii) silane oligomer possessing at least one mercaptosilane unit and at least one blocked mercaptosilane unit, the silicon atoms of adjacent silane units being bonded to each other through a bridging dialkoxy group, the terminal silane units possessing at least one hydroxyalkoxysilyl group or a cyclic dialkoxysilyl group, with the provisio that, where the organofunctional silane composition resulting from step (a) contains one or more of (i), (iii) and (vi), said composition is combined with one or more of (ii), (iv), (v), (vii) and (viii), and where the organofunctional silane composition resulting from step (a) contains one or more of (ii), (iv) and (vii), said composition is combined with one or more of (i), (iii), (v), (vi) and (viii).

As will be appreciated from the foregoing, the composition resulting from the process of this invention can include one or more silane dimers and/or oligomers in which adjacent silane units are bonded to each other through a bridged dialkoxysilane derived from a polyhydroxy-containing compound, e.g., a diol (glycol), triol, tetrol, etc., all of which are low volatile organic compounds (VOCs) relative to simple monohydroxy-containing compounds such as methanol and ethanol which are released by known mercaptosilanes, blocked mercaptosilanes and/or polysulfide silanes.

It will also be appreciated that all of the compositions resulting from the process of the invention contain both mercaptan and blocked mercaptan functionalities, either present in the same silane or in mixtures of individual silanes. While it is known that silanes possessing exclusively mercaptan functionality are prone to scorchiness when used as coupling agents in the manufacture of rubber-based articles such as tires, it has come as a surprise that the compositions of this invention which possess both mercaptan and blocked mercaptan functionalities possess long scorch times, e.g., approaching those of silanes possessing exclusively blocked mercaptan, but with significantly better performance than the latter.

DETAILED DESCRIPTION OF THE INVENTION

The expression "organofunctional silane" as used herein shall be understood to mean a non-polymeric, dimeric or oligomeric silane possessing mercaptan and/or blocked mercaptan functionality and at least one hydroxyalkoxysilyl and/or cyclic dialkoxysilyl group, and, in the case of the dimeric and oligomeric organofunctional silanes, possessing dialkoxy bridging groups linking adjacent silane units.

Organofunctional silanes (i)-(viii) of the present invention and their mixtures can be obtained, inter alia, from one or more silanes of the general formulae:

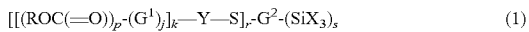   (1)

   (2)

   (3)

wherein:

each occurrence of Y is independently selected from a polyvalent species $(Q)_zA(=E)$, wherein the atom (A) attached to an unsaturated heteroatom (E) is attached to a sulfur, which in turn is linked by means of a group $G^2$ to a silicon atom;

each occurrence of R is independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms, with the proviso that if $G^1$ is univalent, $G^1$ can be hydrogen;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of X is independently selected from the group consisting of —Cl, —Br, RO—, RC(=O)O—, $R_2C=NO$—, $R_2NO$—, $R_2N$—, —R, wherein each R is as above;

each occurrence of Q is independently selected from the group consisting of oxygen, sulfur, and (—NR—);

each occurrence of A is independently selected from the group consisting of carbon, sulfur, phosphorus, and sulfonyl;

each occurrence of E is independently selected from the group consisting of oxygen, sulfur, and (—NR—);

each occurrence of the subscripts, a, b, c, j, k, p, q, r, s, and z are independently given by a is 0 to about 7; b is 1 to about 3; c is 1 to about 6; j is 0 to about 1, but j may be 0 only if p is 1; k is 1 to 2, with the provisos that if A is carbon, sulfur, or sulfonyl, then (i) a+b=2 and (ii) k=1;

if A is phosphorus, then a+b=3 unless both (i) c>1 and (ii) b=1, in which case a=c+1; and if A is phosphorus, then k is 2; p is 0 to 5, q is 0 to 6; r is 1 to 3; s is 1 to 3; z is 0 to about 3 and with the proviso that each of the above structures contains at least one hydrolysable X group.

In one particular embodiment of the invention, the silane reactants are trialkoxysilanes represented by at least one of the general formula:

   (4)

   (5)

wherein each R independently has one of the aforestated meanings and, advantageously, is a methyl, ethyl, propyl, isopropyl, n-butyl, or sec-butyl group; $G^2$ is an alkylene group of from 1 to about 12 carbon atoms; and, $G^1$ is an alkyl group of from 3 to about 12 carbon atoms.

Mixtures of different silane monomers (1, 2 and/or 3) can be used to make the organofunctional silanes, e.g., two or more mercaptotrialkoxysilanes of Formula (5), two or more thiocarboxylate trialkoxysilanes of Formula (4) and mixtures of one or more mercaptotrialkoxysilanes (5) and one or more thiocarboxylate trialkoxysilanes (4) with R, $G^1$ and $G^2$ in these silanes being defined as in silanes (1) and (3).

In a silane dimer or oligomer of this invention, each silane unit of the dimer or oligomer is bonded to an adjacent silane unit through a bridging group resulting from the reaction of the selected silane monomer(s) with one or more polyhydroxy-containing compounds of the general formula:

   (6)

wherein $G^3$ is a hydrocarbon group of from 1 to about 15 carbon atoms or a heterocarbon group of from 4 to about 15 carbon atoms containing one or more etheric oxygen atoms and d is an integer of from 2 to about 8.

In one embodiment of the invention, polyhydroxy-containing compound (6) is a diol (glycol) of at least one of the general formulae:

   (7)

   (8)

wherein $R^0$ is independently given by one of the members listed above for R, f is 2 to about 15 and e is 2 to about 7. Representative examples of such diols are $HOCH_2CH_2OH$, $HOCH_2CH_2CH_2OH$, $HOCH_2CH_2CH_2CH_2OH$, $HOCH_2CH(CH_3)CH_2OH$, etc., a diol possessing an etheric oxygen-containing group such as $HOCH_2CH_2OCH_2CH_2OH$, $HOCH_2CH_2OCH_2CH_2OCH_2CH_2OH$, HOCH$_2$CH$_2$CH$_2$OCH$_2$CH$_2$CH$_2$OH, and a diol possessing a polyether backbone such as a diol of Formula (8) in which R$^0$ is hydrogen or methyl and e is 3 to about 7

In another embodiment of the invention, polyhydroxy-containing compound (5) possesses higher hydroxyl functionality, e.g., a triol or tetrol, of the general formula:

wherein G$^3$ is a is a substituted hydrocarbon group from 2 to about 15 carbon atoms or a substituted heterocarbon from 4 to about 15 carbon atoms and contains one or more etheric oxygen atoms; and d is an integer of from 3 to about 8. Examples of higher hydroxyl functionality compounds (9) include glycerol, trimethylolethane, trimethylolpropane, 1,2,4-butanetriol, 1,2,6-hexanetriol, pentaerythritol, dipentaerythritol, tripentaerythritol, mannitol, galacticol, sorbitol, etc.

Mixtures of polyhydroxy-containing compounds (6) can also be used herein.

Organofunctional silanes (i)-(viii) and mixtures thereof can be prepared by the process which comprises reacting at least one silane of one or more of general formulae (1), (2), and/or (3) supra:

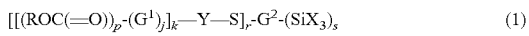

with at least one polyhydroxy-containing compound of the general formula (6):

wherein each occurrence of G$^1$, G$^2$, G$^3$, R, Y, X, a, b, c, d, j, k, p, r, and s are defined supra and with the proviso that at least one of the X is a hydrolyzable group, each of the aforesaid having the meanings previously stated, under transesterification reaction conditions, part or all of the product(s) of the reaction being optionally treated to convert blocked mercaptan functionality, if present, to mercaptan functionality, or to convert mercaptan functionality, if present, to blocked mercaptan functionality.

In a first embodiment of the foregoing process, at least one blocked mercaptosilane (1) or (2) is transesterified with at least one polyhydroxy-containing compound (6), optionally, in the presences of catalyst, e.g., transesterification catalyst, to provide one or more organofunctional blocked mercaptosilanes (ii), (iv) and (vii), part or all of the blocked mercaptosilane(s) thereafter being subjected to partial or complete deblocking to provide one or more organofunctional silanes (i), (iii), (iv), (vi) and (viii), any of which may be in admixture with one or more of (ii), (iv), and (vii) depending on the extent of deblocking.

In one application of this first embodiment of the general preparative process herein, at least one thiocarboxylate trialkoxysilane (4) is transesterified with at least one diol (7) or (8), optionally, in the presence of a transesterification catalyst such as para-toluenesulfonic acid, to provide organofunctional silane (vii), i.e., blocked mercaptosilane oligomer, which can thereafter be subjected to partial deblocking employing a suitable base such as alkali metal alkoxide, e.g., sodium ethoxide in ethanol, to yield one or more organofunctional silanes (viii), i.e., silane oligomer containing one or more mercaptosilanes and one or more blocked mercaptosilanes, alone or in combination with one or more other organofunctional silanes (i)-(vi).

In a second embodiment of the general preparative procedure herein, at least one mercaptosilane (3) in admixture with at least one blocked mercaptosilane (1) or (2) are transesterified with at least one polyhydroxy-containing compound (6), optionally, in the presence transesterification catalyst, to provide, inter alia, one or more organofunctional silanes (v) and/or (viii), and/or other mixtures of organofunctional silanes, e.g., a mixture of silanes (i) and (ii), (i) and (v), (i), (ii) and (v), (i), (ii) and (v), (ii) and (v), (ii) and (viii), (v) and (viii), (i), (ii), (v) and (viii), etc.

In one application of the foregoing second embodiment of the general preparative process, at least one mercaptotrialkoxysilane (5) and at least one thiocarboxylate trialkoxysilane (4) are transesterified together with at least one diol (7), optionally, in the presence of transesterification catalyst, to provide one or more silanes (v) and/or (viii) which, if desired, can be subjected to deblocking to increase the amounts of mercaptosilane relative to blocked mercaptosilane in a particular silane product or mixture of silane products.

In a third embodiment of the general preparative process, at least one mercaptosilane (3) is transesterified with at least one polyhydroxy-containing compound (6), optionally, in the presence of transesterification catalyst, to provide at least one dimer (iii) and/or oligomer (vi), or mercaptosilane (i) alone or in admixture with dimer (iii) and/or oligomer (iv). Optionally, any of these transesterification products or their mixtures can be subjected to esterification with a carboxylic acid or acid halide to block mercapto groups therein.

In one application of the foregoing third embodiment of the general preparative process, at least one mercaptotrialkoxysilane (5) is transesterified with at least one diol (7), optionally, in the presence of transesterification catalyst, to provide mercaptosilane dimer (iii) and/or oligomer (vi).

It is also within the scope of the invention to combine part or all of the esterification product(s) obtained from one of the aforedescribed process embodiments with part or all of the product(s) obtained from one of the other process embodiments. Thus, e.g., blocked mercaptosilane dimer (iv) and/or blocked mercaptosilane oligomer (vii) resulting from the first preparative procedure can be admixed with mercaptosilane dimer (iii) and/or mercaptosilane oligomer (vi) to provide a mixture of organofunctional silanes possessing both mercaptan and blocked mecaptan functionalities. In a similar manner, simple mixing of the esterified product(s) of one particular embodiment of the general preparative process can be admixed with the esterified product(s) of another embodiment of the general preparative process to provide still other compositions within the scope of the invention possessing both mercaptan and blocked mercaptan functionality.

Reaction conditions for the process of preparing organofunctional silanes (i)-(viii) and their mixtures include molar ratios of silane(s), determined by adding the individual molar contribution of silanes (1), (2) and (3), and polyhydroxy-containing compound(s) (6) of from about 0.1 to about 3 moles of (6) per mole of silyl group, determined by adding the individual contribution of silanes (1), (2) and (3), a temperature of from about 0° C. to about 150° C., a pressure of from about 0.1 to about 2,000 mmHg, and in the optional presence of catalyst, solvent, etc.

In a specific embodiment of the present invention, an organofunctional and cyclic and/or bridging dialkoxy silane com position is provided comprising at least one silane selected from the group consisting of:

$$[[[(ROC(=O))_p\text{-}(G^1)_j]_k\text{—Y—S}]_r\text{-}G^2\text{-}(SiX_uZ^b_vZ^c_w)_s]_m \\ [(HS)_r\text{-}G^2\text{-}(SiX_uZ^b_vZ^c_w)_s]_n \quad (10)$$

and $$[[(X_vZ^b_vZ^c_wSi)_q\text{-}G^2]_a\text{-}[Y\text{—}[S\text{-}G^2SiX_uZ^b_vZ^c_w]_b]_c]_m \\ [(HS)_r\text{-}G^2\text{-}(SiX_uZ^b_vZ^c_w)_s]_n \quad (11)$$

wherein:

each occurrence of Y is independently selected from a polyvalent species $(Q)_zA(=E)$, wherein the atom (A) attached to an unsaturated heteroatom (E) is attached to a sulfur, which in turn is linked by means of a group $G^2$ to a silicon atom;

each occurrence of R is independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms, with the proviso that if $G^1$ is univalent, $G^1$ can be hydrogen;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of X is independently selected from the group consisting of —Cl, —Br, RO—, RC(=O)O—, $R_2C=NO—$, $R_2NO—$, $R_2N—$, —R, $HO(R^0CR^0)_fO—$, wherein each R is as above and each occurrence of $R^0$ is independently given by one of the members listed above for R;

each occurrence of $Z^b$, which forms a bridging structure between two silicon atoms, is independently selected from the group consisting of $(—O—)_{0.5}$ and $[—O(R^0CR^0)_fO—]_{0.5}$, wherein each occurrence of $R^0$ is independently given by one of the members listed above for R;

each occurrence of $Z^c$, which forms a cyclic structure with a silicon atom, is independently given by $—O(R^0CR^0)_fO—$ wherein each occurrence of $R^0$ is independently given by one of the members listed above for R;

each occurrence of Q is independently selected from the group consisting of oxygen, sulfur, and (—NR—);

each occurrence of A is independently selected from the group consisting of carbon, sulfur, phosphorus, and sulfonyl;

each occurrence of E is independently selected from the group consisting of oxygen, sulfur, and (—NR—);

each occurrence of the subscripts, a, b, c, f j, k, m, n, p, q, r, s, u, v, w, and z is independently given by a is 0 to about 7; b is 1 to about 3; c is 1 to about 6; f is about 2 to about 15, j is 0 to about 1, but j may be 0 only if p is 1; k is 1 to 2, with the provisos that if A is carbon, sulfur, or sulfonyl, then (i) a+b=2 and (ii) k=1;

if A is phosphorus, then a+b=3 unless both (i) c>1 and (ii) b=1, in which case a=c+1; and if A is phosphorus, then k is 2; m is 1 to about 20, n is 1 to about 20, p is 0 to 5, q is 0 to 6; r is 1 to 3; s is 1 to 3; u is 0 to 3; v is 0 to 3; w is 0 to 1 with the proviso that u+v+2w=3; z is 0 to about 3; and with the proviso that the each of the above structures contains at least one hydrolysable group, $Z^b$ or $Z^c$, that is a difunctional alkoxy group.

In accordance with another embodiment of the present invention, a process for the preparation of an organofunctional silane containing cyclic hydroxyalkyloxysilyl groups, and/or bridging dialkoxysilyl groups and both free and blocked mercaptan functionality groups is provided which comprises blending at least one blocked mercaptofunctional silane of the formula:

$$[[[(ROC(=O))_p\text{-}(G^1)_j]_k\text{—Y—S}]_r\text{-}G^2\text{-}(SiX_3)_s \quad (1)$$

and/or of the formula:

$$[(X_3Si)_q\text{-}G^2]_a\text{-}[Y\text{—}[S\text{-}G^2\text{-}SiX_3]_b]_c \quad (2)$$

with at least one mercaptofunctional silane of the formula:

$$(HS)_r\text{-}G^2\text{-}(SiX_3)_s \quad (3)$$

wherein each occurrence of $G^1$, $G^2$, R, Y, X, a, b, c, j, k, p, q, r, and s have one of the aforestated meanings and with the proviso that at least one of X is a hydrolyzable group, and transesterifying the mixture with a diol $HO(R^0CR^0)_fOH$, advantageously in the presence of a transesterification catalyst wherein $R^0$ and f have one of the aforestated meanings.

In still another embodiment of the invention, a process for the preparation of an organofunctional silane containing cyclic and/or bridging dialkoxy silyl groups and both free and blocked mercaptan functionality is provided which comprises reacting a cyclic and/or bridging dialkoxysilane with a metal alkoxide.

As used herein in connection with silanes (10) and (11), the terms "diol" and "difunctional alcohol" refer to any structure of the general Formula (7):

$$HO(R^0CR^0)_fOH \quad (7)$$

wherein f and $R^0$ are as defined above. These structures represent hydrocarbons in which two hydrogen atoms are replaced with —OH in accordance with compounds (7), supra.

As used herein in connection with silanes (10) and (11), "dialkoxy" and "difunctional alkoxy" refer to hydrocarbon-based diols in which the two OH hydrogen atoms have been removed to give divalent radicals, and whose structures are represented by the general formula:

$$—O(R^0CR^0)_fO— \quad (12)$$

wherein f and $R^0$ are as defined above.

As used herein in connection with silanes (10) and (11), "cyclic dialkoxy" refers to a silane or group in which cyclization is about a silicon atom by two oxygen atoms each of which is attached to a common divalent hydrocarbon group such as is commonly the case with diols. Cyclic dialkoxy groups herein are represented by $Z^c$. The structure of $Z^c$ is important in the formation of the cyclic structure. $R^0$ groups that are more sterically hindered than hydrogen promote the formation of cyclic structures. The formation of cyclic structures is also promoted when the value of f in diol (7) is 2 or 3, and more preferably 3.

As used herein in connection with silanes (10) and (11), "bridging dialkoxy" refers to a silane or group in which two different silicon atoms are each bound to one oxygen atom, which in turn is bound to a common divalent hydrocarbon group such as is commonly found in diols. Bridging dialkoxy groups herein are represented by $Z^b$.

As used herein in connection with silanes (10) and (11), "hydroxyalkoxy" refers to a silane or group in which one OH hydrogen atom has been removed to provide a monovalent radical, and whose structures are represented by the general formula:

$$HO(R^0CR^0)_fO— \quad (13)$$

wherein f and $R^O$ are defined above. Hydroxyalkoxy groups herein are represented by X.

As used herein in connection with silanes (10) and (11), the term "hydrocarbon based diols" refers to diols that contain two OH groups as part of a hydrocarbon structure. Absent from these hydrocarbon based diols are heteroatoms (other than, of course, the oxygens in the OH groups), in particular ether groups, which are deliberately avoided due to problems associated with their tendency to spontaneously form peroxides which may lead to flammability hazards and free radical formation.

The structure (7) will be referred to herein as the appropriate diol (in a few specific cases, glycol is the more commonly used term), prefixed by the particular hydrocarbon group associated with the two OH groups. Examples include neopentylglycol, 1,3-butanediol, and 2-methyl-2,4-pentanediol.

The structure (12) will be referred to herein as the appropriate dialkoxy, prefixed by the particular hydrocarbon group associated with the two OH groups. Thus, for example, the diols, neopentylglycol, 1,3-butanediol, and 2-methyl-2,4-pentanediol correspond herein to the dialkoxy groups, neopentylglycoxy, 1,3-butanedialkoxy, and 2-methyl-2,4-pentanedialkoxy, respectively.

The silanes herein that contain both a free and blocked mercaptofunctional group, in which the diol from which such silanes are derived is commonly referred to as a glycol, are named as the corresponding glycoxysilane. Cyclic dialkoxy silanes herein, in which the diol from which the silane is derived is commonly referred to as a diol, are named as the corresponding dialkoxysilane.

As used herein for $Z^b$, the notations, $(-O-)_{0.5}$ and $[-O(R^OCR^O)_fO-]_{0.5}$, refer to one-half of a siloxane bond, and one-half of a bridging dialkoxy group, respectively. These notations are used in conjunction with a silicon atom and they are taken herein to mean one-half of an oxygen atom, namely, the half bound to the particular silicon atom, or to one-half of a dialkoxy group, namely, the half bound to the particular silicon atom, respectively. It is understood that the other half of the oxygen atom or dialkoxy group and its bond to silicon occurs somewhere else in the overall molecular structure being described. Thus, the $(-O-)_{0.5}$ siloxane groups and the $[-O(R^OCR^O)_fO-]_{0.5}$ dialkoxy groups mediate the chemical bonds that hold two separate silicon atoms together, whether these two silicon atoms occur intermolecularly or intramolecularly. In the case of $[-O(R^OCR^O)_fO-]_{0.5}$, if the hydrocarbon group $(R^OCR^O)_f$ is unsymmetrical, either end of $[-O(R^OCR^O)_fO-]_{0.5}$ may be bound to either of the two silicon atoms required to complete the structures of silanes (10) and (11).

As used herein in connection with silanes (1), (2), (3), (10) and (11), "alkyl" includes straight, branched and cyclic alkyl groups; "alkenyl" includes any straight, branched, or cyclic alkenyl group containing one or more carbon-carbon double bond, where the point of substitution can be either at a carbon-carbon double bond or elsewhere in the group; and "alkynyl" includes any straight, branched, or cyclic alkynyl group containing one or more carbon-carbon triple bonds and, optionally, one or more carbon-carbon double bonds as well, where the point of substitution can be either at a carbon-carbon triple bond, a carbon-carbon double bond, or elsewhere in the group. Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of alkynyls include, but are not limited to, acetylenyl, propargyl and methylacetylenyl.

As used herein in connection with silanes (1), (2), (3), (10)) and (11), "aryl" includes any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Specific examples of aryls include, but are not limited to, phenyl and naphthalenyl. Specific examples of aralkyls include, but are not limited to, benzyl and phenethyl. Specific examples of arenyls include, but are not limited to, tolyl and xylyl.

As used herein in connection with silanes (1), (2), (3), (10) and (11), "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

Representative examples of the functional groups (—YS—) present in the silanes of the present invention include, but are not limited to, thiocarboxylate ester, —C(=O)—S— (any silane with this functional group is a "thiocarboxylate ester silane"); dithiocarboxylate, —C(=S)—S— (any silane with this functional group is a "dithiocarboxylate ester silane"); thiocarbonate ester, —O—C(=O)—S— (any silane with this functional group is a "thiocarbonate ester silane"); dithiocarbonate ester, —S—C(=O)—S— and —O—C(=S)—S— (any silane with this functional group is a "dithiocarbonate ester silane"); trithiocarbonate ester, —S—C(=S)—S— (any silane with this functional group is a "trithiocarbonate ester silane"); dithiocarbamate ester, N—C(=S)—S— (any silane with this functional group is a "dithiocarbamate ester silane"); thiosulfonate ester, —S(=O)$_2$—S— (any silane with this functional group is a "thiosulfonate ester silane"); thiosulfate ester, —O—S(=O)$_2$—S— (any silane with this functional group is a "thiosulfate ester silane"); thiosulfamate ester, (—N—)S(=O)$_2$—S— (any silane with this functional group is a "thiosulfamate ester silane"); thiosulfinate ester, C—S(=O)—S— (any silane with this functional group is a "thiosulfinate ester silane"); thiosulfite ester, —O—S(=O)—S— (any silane with this functional group is a "thiosulfite ester silane"); thiosulfimate ester, N—S(=O)—S— (any silane with this functional group is a "thiosulfimate ester silane"); thiophosphate ester, P(=O)(O—)$_2$(S—) (any silane with this functional group is a "thiophosphate ester silane"); dithiophosphate ester, P(=O)(O—)(S—)$_2$ or P(=S)(O—)$_2$(S—) (any silane with this functional group is a "dithiophosphate ester silane"); trithiophosphate ester, P(=O)(S—)$_3$ or P(=S)(O—)(S—)$_2$ (any silane with this functional group is a "trithiophosphate ester silane"); tetrathiophosphate ester P(=S)(S—)$_3$ (any silane with this functional group is a "tetrathiophosphate ester silane"); thiophosphamate ester, —P(=O)(—N—)(S—) (any silane with this functional group is a "thiophosphamate ester silane"); dithiophosphamate ester, —P(=S)(—N—)(S—) (any silane with this functional group is a "dithiophosphamate ester silane"); thiophosphoramidate ester, (—N—)P(=O)(O—)(S—) (any silane with this functional group is a "thiophosphoramidate ester silane"); dithiophosphoramidate ester, (—N—)P(=O)(S—)$_2$ or (—N—)P(=S)(O—)(S—) (any silane with this functional group is a "dithiophosphoramidate ester silane"); and trithiophosphoramidate ester, silane").

In another embodiment, each occurrence of Y is selected independently from the group consisting of —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)$_2$—; (—NR)S(=O)—; —SS(=O)$_2$—; (—S)$_2$P(=O)—; —(—S)P(=O)—; —P(=O)(-)$_2$; (—S)$_2$P(=S)—; —(—S)P(=S)—; —P(=S)(-)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and, —(—NR)P(=S)—.

In still another embodiment, Y is —C(=O)—.

In another embodiment of the present invention, the novel silane is one in which Y is —C(=O)—, G$^1$ has a primary carbon atom attached to the carbonyl and is a C$_1$-C$_{18}$ alkyl, and G$^2$ is a divalent or polyvalent group derived by substitution of C$_1$-C$_{12}$ alkyl.

In still another embodiment of the present invention, the novel silane is one in which Y is —C(=O)—, G$^1$ is a monovalent straight chain group derived from a C$_3$-C$_{10}$, alkyl, and G$^2$ is a divalent or polyvalent group derived by substitution of a C$_3$-C$_{10}$ alkyl, p is 0, j is 1 and k is 1 and the ratio of m to n is in the range of about 20:1 to 3:1.

In yet another embodiment of the present invention, the novel silane is one in which Y is —C(=O)—, G$^1$ is a monovalent straight chain group derived from a C$_6$-C$_8$ alkyl, G is a divalent or polyvalent group derived by substitution of a C$_3$-C$_6$ alkyl, p is 0, j is 1 and k is 1 and the ratio of m to n is in the range of about 10:1 to about 4:1.

Representative examples of G$^1$ include, but are not limited to, CH$_3$(CH$_2$)$_g$—, wherein g is 1 to about 29; benzyl; 2-phenylethyl; diethylene cyclohexane; 1,2,4-triethylene cyclohexane; diethylene benzene; phenylene; —(CH$_2$)$_g$— wherein g is preferably 1 to 29, which represent the terminal straight-chain alkyls further substituted terminally at the other end, such as —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their beta-substituted analogs, such as —CH$_2$(CH$_2$)$_i$CH(CH$_3$)—, where i is preferably 0 to 16; —CH$_2$CH$_2$C(CH$_3$)$_2$CH$_2$—; the structure derivable from methallyl chloride, —CH$_2$CH(CH$_3$)CH$_2$—; any of the structures derivable from divinylbenzene, such as —CH$_2$CH$_2$(C$_6$H$_4$)CH$_2$CH$_2$— and —CH$_2$CH$_2$(C$_6$H$_4$)CH(CH$_3$)—, where the notation C$_6$H$_4$ denotes a disubstituted benzene ring; any of the structures derivable from dipropenylbenzene, such as —CH$_2$CH(CH$_3$)(C$_6$H$_4$)CH(CH$_3$)CH$_2$—, where the notation C$_6$H$_4$ denotes a disubstituted benzene ring; any of the structures derivable from butadiene, such as —CH$_2$CH$_2$CH$_2$CH$_2$—, —CH$_2$CH$_2$CH(CH$_3$)—, and —CH$_2$CH(CH$_2$CH$_3$)—; any of the structures derivable from piperylene, such as —CH$_2$CH$_2$CH$_2$CH(CH$_3$)—, —CH$_2$CH$_2$CH(CH$_2$CH$_3$)—, and —CH$_2$CH(CH$_2$CH$_2$CH$_3$)—; any of the structures derivable from isoprene, such as —CH$_2$CH(CH$_3$)CH$_2$CH$_2$—, —CH$_2$CH(CH$_3$)CH(CH$_3$)—, —CH$_2$C(CH$_3$)(CH$_2$CH$_3$)—, —CH$_2$CH$_2$CH(CH$_3$)CH$_2$—, —CH$_2$CH$_2$C(CH$_3$)$_2$— and —CH$_2$CH[CH(CH$_3$)$_2$]—; any of the isomers of —CH$_2$CH$_2$-norbornyl-, —CH$_2$CH$_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, —CH$_2$CH(4-CH$_3$-1-C$_6$H$_9$—)CH$_3$, where the notation C$_6$H$_9$ denotes isomers of the trisubstituted cyclohexane ring lacking substitution in the 2 position; any of the monovinyl-containing structures derivable from trivinylcyclohexane, such as —CH$_2$CH$_2$(vinylC$_6$H$_9$)CH$_2$CH$_2$— and —CH$_2$CH$_2$(vinylC$_6$H$_9$)CH(CH$_3$)—, where the notation C$_6$H$_9$ denotes any isomer of the trisubstituted cyclohexane ring; any of the monounsaturated structures derivable from myrcene containing a trisubstituted C=C, such as —CH$_2$CH[CH$_2$CH$_2$CH=C(CH$_3$)$_2$]CH$_2$CH$_2$—, —CH$_2$CH[CH$_2$CH$_2$CH=C(CH$_3$)$_2$]CH(CH$_3$)—, —CH$_2$C[CH$_2$CH$_2$CH=C(CH$_3$)$_2$](CH$_2$CH$_3$)—, —CH$_2$CH$_2$CH[CH$_2$CH$_2$CH=C(CH$_3$)$_2$]CH$_2$—, —CH$_2$CH$_2$(C—)(CH$_3$)[CH$_2$CH$_2$CH=C(CH$_3$)$_2$], and —CH$_2$CH[CH(CH$_3$)[CH$_2$CH$_2$CH=C(CH$_3$)$_2$]]—; and, any of the monounsaturated structures derivable from myrcene lacking a trisubstituted C=C, such as —CH$_2$CH(CH=CH$_2$)CH$_2$CH$_2$CH$_2$C(CH$_3$)$_2$—, —CH$_2$CH(CH=CH$_2$)CH$_2$CH$_2$CH[CH(CH$_3$)$_2$]—, —CH$_2$C(=CH—CH$_3$)CH$_2$CH$_2$CH$_2$C(CH$_3$)$_2$—, —CH$_2$C(=CH—CH$_3$)CH$_2$CH$_2$CH[CH(CH$_3$)$_2$]—, —CH$_2$CH$_2$C(=CH$_2$)CH$_2$CH$_2$CH$_2$C(CH$_3$)$_2$—, —CH$_2$CH$_2$C(=CH$_2$)CH$_2$CH$_2$CH[CH(CH$_3$)$_2$]—, —CH$_2$CH=C(CH$_3$)$_2$CH$_2$CH$_2$C(CH$_3$)$_2$—, and —CH$_2$CH=C(CH$_3$)$_2$CH$_2$CH$_2$CH[CH(CH$_3$)$_2$].

Representative examples of G$^2$ include, but are not limited to, diethylene cyclohexane; 1,2,4-triethylene cyclohexane; diethylene benzene; phenylene; —(CH$_2$)$_g$— wherein g is preferably 1 to 29, which represent terminal straight-chain alkyls further substituted terminally at the other end, such as —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their beta-substituted analogs, such as —CH$_2$(CH$_2$)$_i$CH(CH$_3$)—, where i is preferably 0 to 16; —CH$_2$CH$_2$C(CH$_3$)$_2$CH$_2$—; the structure derivable from methallyl chloride, —CH$_2$CH(CH$_3$)CH$_2$—; any of the structures derivable from divinylbenzene, such as —CH$_2$CH$_2$(C$_6$H$_4$)CH$_2$CH$_2$— and —CH$_2$CH$_2$(C$_6$H$_4$)CH(CH$_3$)—, where the notation C$_6$H$_4$ denotes a disubstituted benzene ring; any of the structures derivable from dipropenylbenzene, such as —CH$_2$CH(CH$_3$)(C$_6$H$_4$)CH(CH$_3$)CH$_2$—, where the notation C$_6$H$_4$ denotes a disubstituted benzene ring; any of the structures derivable from butadiene, such as —CH$_2$CH$_2$CH$_2$CH$_2$—, —CH$_2$CH$_2$CH(CH$_3$)—, and —CH$_2$CH(CH$_2$CH$_3$)—; any of the structures derivable from piperylene, such as —CH$_2$CH$_2$CH$_2$CH(CH$_3$)—, —CH$_2$CH$_2$CH(CH$_2$CH$_3$)—, and —CH$_2$CH(CH$_2$CH$_2$CH$_3$)—; any of the structures derivable from isoprene, such as —CH$_2$CH(CH$_3$)CH$_2$CH$_2$—, —CH$_2$CH(CH$_3$)CH(CH$_3$)—, —CH$_2$C(CH$_3$)(CH$_2$CH$_3$)—, —CH$_2$CH$_2$CH(CH$_3$)CH$_2$—, —CH$_2$CH$_2$C(CH$_3$)$_2$— and —CH$_2$CH[CH(CH$_3$)$_2$]—; any of the isomers of —CH$_2$CH$_2$-norbornyl-, —CH$_2$CH$_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, —CH$_2$CH(4-CH$_3$-1-C$_6$H$_9$—)CH$_3$, where the notation C$_6$H$_9$ denotes isomers of the trisubstituted cyclohexane ring lacking substitution in the 2 position; any of the monovinyl-containing structures derivable from trivinylcyclohexane, such as —CH$_2$CH$_2$(vinylC$_6$H$_9$)CH$_2$CH$_2$— and —CH$_2$CH$_2$(vinylC$_6$H$_9$)CH(CH$_3$)—, where the notation C$_6$H$_9$ denotes any isomer of the trisubstituted cyclohexane ring; any of the monounsaturated structures derivable from myrcene containing a trisubstituted C=C, such as —CH$_2$CH[CH$_2$CH$_2$CH=C(CH$_3$)$_2$]CH$_2$CH$_2$—, —CH$_2$CH[CH$_2$CH$_2$CH=C(CH$_3$)$_2$]CH(CH$_3$)—, —CH$_2$C[CH$_2$CH$_2$CH=C(CH$_3$)$_2$](CH$_2$CH$_3$)—, —CH$_2$CH$_2$CH[CH$_2$CH$_2$CH=C(CH$_3$)$_2$]CH$_2$—, —CH$_2$CH$_2$(C—)(CH$_3$)

[CH$_2$CH$_2$CH=C(CH$_3$)$_2$], and —CH$_2$CH[CH(CH$_3$) [CH$_2$CH$_2$CH=C(CH$_3$)$_2$]]—; and any of the monounsaturated structures derivable from myrcene lacking a trisubstituted C=C, such as —CH$_2$CH(CH=CH$_2$) CH$_2$CH$_2$CH$_2$C(CH$_3$)$_2$—, —CH$_2$CH(CH=CH$_2$) CH$_2$CH$_2$CH[CH(CH$_3$)$_2$]—, —CH$_2$C(=CH—CH$_3$) CH$_2$CH$_2$CH$_2$C(CH$_3$)$_2$—, —CH$_2$C(=CH—CH$_3$) CH$_2$CH$_2$CH[CH(CH$_3$)$_2$]—, —CH$_2$CH$_2$C(=CH$_2$) CH$_2$CH$_2$CH$_2$C(CH$_3$)$_2$—, —CH$_2$CH$_2$C(=CH$_2$)CH$_2$CH$_2$CH [CH(CH$_3$)$_2$]—, —CH$_2$CH=C(CH$_3$)$_2$CH$_2$CH$_2$CH$_2$C (CH$_3$)$_2$— and —CH$_2$CH=C(CH$_3$)$_2$CH$_2$CH$_2$CH[CH (CH$_3$)$_2$].

In another embodiment of the present invention, the silane (10) has a structure in which the sum of the carbon atoms in its G$^1$ and G$^2$ groups is from 3 to 18 and, advantageously, is from 6 to 14. The amount of carbon in the blocked mercapto fragment facilitates the dispersion of the inorganic filler into the organic polymers, thereby improving the balance of properties in the cured filled rubber.

In yet another embodiment of the present invention, G$^1$ is —CH$_3$CH$_2$CH$_2$CH$_2$CH$_2$CH$_2$CH$_2$— and G$^2$ is —CH$_2$CH$_2$CH$_2$—, r is 1 and s is 1.

Representative examples of R and R$^0$ groups are hydrogen, branched and straight-chain alkyls of 1 to 18 carbon atoms or more, such as methyl, ethyl, propyl, isopropyl, butyl, octenyl, cyclohexyl, phenyl, benzyl, tolyl and allyl.

In one embodiment, R groups are selected from C$_1$ to C$_4$ alkyls and hydrogen and R$^0$ groups are selected from hydrogen, methyl, ethyl and propyl.

Specific examples of X are methoxy, ethoxy, isobutoxy, propoxy, isopropoxy, acetoxy, oximato and monovalent hydroxyalkoxy groups derived from diols, —O(R$^0$CR$^0$)$_f$OH where f is defined above, such as 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydoxybut-1-oxy. X may also be a monovalent alkyl group, such as methyl and ethyl.

In a specific embodiment, X is one of methoxy, ethoxy, acetoxy, methyl, ethyl, 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydoxybut-1-oxy.

Specific examples of Z$^b$ and Z$^c$ are the divalent alkoxy groups derived from diols such as ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol and pinacol. The divalent alkoxy groups derived from ethylene glycol, propylene glycol, neopentyl glycol, 1,3-propanediol, 2-methyl-1,3-propanediol, 1,3-butanediol and 2-methyl-2,4-pentanediol are preferred.

In an embodiment of the present invention, the Z$^b$ and Z$^c$ are divalent alkoxy groups derived from 1,3-propanediol, 2-methyl-1,3-propanediol, 1,3-butanediol, and 2-methyl-2,4-pentanediol.

The cyclic dialkoxy content of the silanes herein should be kept sufficiently high relative to the total dialkoxy content present to prevent excessive crosslinking, which would lead to gellation. Excessive crosslinking can also be avoided if X in the structure, as indicated by the coefficient u, is large. In one embodiment, the v and w in Formulae (10) and (11) are such that the ratio v/w is between 0 and 10. In another embodiment, u is from 1 to about 2 with the proviso that u+v+2w=3.

Representative examples of the organofunctional silanes of the present invention that contain cyclic and/or bridging dialkoxysilyl groups and free and blocked mercapto groups include, but are not limited to, thioacetic acid 2-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-ethyl ester; thioacetic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; thiobutyric acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid S-[3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl)-propyl]ester; octanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl] ester; undecanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; heptanethioic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; heptanethioic acid S-[3-(2-{3-[(3-hydroxy-2-methyl-propoxy)-(3-mercapto-propyl)-methyl-silanyloxy]-2-methyl-propoxy}-5-methyl-[1,3,2]dioxasilepan-2-yl)-propyl]ester; thiopropionic acid 3-{2-[3-((3-mercapto-propyl)-methyl-{2-methyl-3-[5-methyl-2-(3-propionylsulfanyl-propyl)-[1,3,2] dioxasilinan-2-yloxy]-propoxy}-silanyloxy)-2-methyl-propoxy]-5-methyl-[1,3,2]dioxasilepan-2-yl}-propyl ester; octanethioic acid 3-{2-[3-((3-mercapto-propyl)-methyl-{2-methyl-3-[5-methyl-2-(3-octanoylsulfanyl-propyl)-[1,3,2] dioxasilinan-2-yloxy]-propoxy}-silanyloxy)-2-methyl-propoxy]-5-methyl-[1,3,2]dioxasilepan-2-yl}-propyl ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-methyl-(3-octanoylsulfanyl-propyl)-silanyloxy]-2-methyl-propoxy}-methyl-silanyl)-propyl]ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-(3-mercapto-propyl)-methyl-silanyloxy]-2-methyl-propoxy}-methyl-silanyl)-propyl]ester; octanethioic acid S-[3-((3-hydroxy-2-methyl-propoxy)-{3-[{3-[bis-(3-hydroxy-2-methyl-propoxy)-(3-mercapto-propyl)-silanyloxy]-2-methyl-propoxy}-(3-mercapto-propyl)-(3-hydroxy-2-methyl-propoxy)-silanyloxy]-2-methyl-propoxy}-(3-hydroxy-2-methyl-propoxy)-silanyl)-propyl] ester; dimethyl-thiocarbamic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; dimethyl-dithiocarbamic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; dimethyl-dithiocarbamic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; thiocarbonic acid O-ethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; trithiocarbonic acid ethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; trithiocarbonic acid ethyl ester 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; dithiobutyric acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; dithiobutyric acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; diethyl-dithiocarbamic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; diethyl-dithiocarbamic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; N-methyl-thiobutyrimidic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; N-methyl-thiobutyrimidic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; thiophosphoric acid O,O'-diethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; thiophosphoric acid O-ethyl ester S-[3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl]ester O'-propyl ester; dithiophosphoric acid O-ethyl ester S-[3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl]ester O'-propyl ester; trithiophosphoric acid S,S'-diethyl ester S''-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; tetrathiophosphoric acid diethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; tetrathiophosphoric acid diethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; tetrathiophosphoric acid ethyl ester 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester propyl ester; methyl-phosphonodithioic acid S-ethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; dimethyl-phosphinothioic acid S-[3-((3-hydroxy-2-methyl-propoxy)-{3-[(3-hydroxy-2 methyl-propoxy)-(3-mercapto-propyl)-methyl-silanyloxy]-2-methyl-propoxy}-methyl-silanyl)-propyl]ester, and the like.

In another embodiment, the cyclic and bridging dialkoxy free and blocked mercapto functional silanes of the present invention include, but are not limited to, octanethioic acid S-[3-((3-hydroxy-2-methyl-propoxy)-{3-[{3-[bis-(3-hydroxy-2-methyl-propoxy)-(3-mercapto-propyl)-silanyloxy]-2-methyl-propoxy}-(3-mercapto-propyl)-(3-hydroxy-2-methyl-propoxy)-silanyloxy]-2-methyl-propoxy}-(3-hydroxy-2-methyl-propoxy)-silanyl)-propyl]ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-(3-mercapto-propyl)-methyl-silanyloxy]-2-methyl-propoxy}-methyl-silanyl)-propyl]ester; octanethioic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid S-[3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl)-propyl]ester; octanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; undecanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; heptanethioic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; heptanethioic acid S-[3-(2-{(3-hydroxy-2-methyl-propoxy)-(3-mercapto-propyl)-methyl-silanyloxy]-2-methyl-propoxy}-5-methyl-[1,3,2]dioxasilepan-2-yl)-propyl]ester; thiopropionic acid 3-{2-[3-((3-mercapto-propyl)-methyl-{2-methyl-3-[5-methyl-2-(3-propionylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester; and octanethioic acid 3-{2-[3-((3-mercapto-propyl)-methyl-{2-methyl-3-[5-methyl-2-(3-octanoylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester.

The organofunctional silane compositions of this invention that contain cyclic and/or bridging silyl groups and both free and blocked mercaptan groups normally have a random distribution of free and blocked mercapto groups within the individual silane. However, silanes in accordance with the invention can be prepared in which the free and blocked mercaptan groups are segregated. This segregation will result in compositions where the nearest neighbors to a free mercaptan group are other free mercaptan groups or the nearest neighbors to a blocked mercaptan group are other blocked mercaptan groups. The segregation of the free and blocked mercaptan groups can occur when blocked mercaptofunctional cyclic and bridged silanes are physically mixed with free mercaptofunctional cyclic and bridged silanes.

Moreover, it is understood that these novel silane compositions can also contain free and blocked mercaptofunctional silane components that contain only monofunctional alkoxy groups. These free and blocked mercaptofunctional silanes containing only monofunctional alkoxy groups may be used as reagents in the preparation of the novel silanes of the present invention. However, it is understood that these monofunctional alkoxy groups may contribute to VOC emissions during use. Moreover, it is understood that the partial hydrolyzates and/or condensates of these cyclic and bridging dialkoxy blocked mercaptofunctional silanes (i.e., cyclic and bridging dialkoxy blocked mercaptofunctional siloxanes and/or silanols) may also be encompassed by the silanes herein, in that these partial hydrolyzates and/or condensates will be a side product of most methods of manufacture of the novel silanes of the present invention or can occur upon storage, especially in humid conditions, or under conditions in which residual water remaining from their preparation is not completely removed subsequent to their preparation.

Furthermore, partial to substantial hydrolysis of silanes (10) and (11) will form novel silanes that contain siloxane bonds, i.e., $Z^b=(-O-)_{0.5}$, and are encompassed by the silanes described herein. They can be deliberately prepared by incorporating the appropriate stoichiometry or an excess of water into the methods of preparation described herein for the silanes. Silane structures herein encompassing hydrolyzates and siloxane are described in the structures represented by Formulae (10) and (11) wherein the subscripts, v, of $Z^b=(-O-)_{0.5}$ and/or u of X=OH are substantive (i.e., substantially larger than zero). In one embodiment of the present invention, the ratio of siloxane bridging group, (—O—)$_{0.5}$, to dioxy bridging group, [—O(R$^0$CR$^0$)$_j$O—]$_{0.5}$, is within a range of from about 0 to about 1. In another embodiment, the ratio is within a range of from about 0 to about 0.2.

In another embodiment of the present invention, the organofunctional silanes herein, including their mixtures, can be loaded on a particulate carrier such as a porous polymer, carbon black, a siliceous material such as or silica, etc., so that they are in solid form for addition to rubber in a rubber compounding operation.

Organofunctional silanes (10) and (11) herein and mixtures thereof can be prepared by the general preparative process described above of which there are numerous specific embodiments. Generally, the process embodiments for making one or a mixture of silanes (10) and (11) involve a transesterification reaction between one or more alkoxysilane formulae (1), (2) and (3) and one or more polyhydroxy-containing compounds of formula (6).

In one embodiment, the process for preparing the organofunctional silanes (10) and/or (11) comprises:

a) transesterifying at least one blocked mercaptofunctional silane:

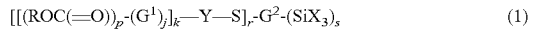

(1)

or

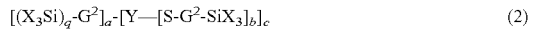

(2)

wherein each occurrence of G$^1$, G$^2$, R, Y, X, a, b, c, j, k, p, q, r, and s are defined supra, and with the proviso that at least one of X is a hydrolyzable group, with at least one diol having the structure HO(R$^0$CR$^0$)$_j$OH, optionally in the presence of a transesterification catalyst; and, b) partially removing blocking groups, e.g., by the addition of a strong base, to provide free mercaptan groups.

The first reaction can be carried out by reacting a mixture of blocked mercaptofunctional alkoxy silane and a diol at a molar ratio of about 0.1 mole to about 3.0 moles of diol per 1 mole of silyl group to be transesterified. In another embodiment, the ratio can range from about 1.0 to about 2.5 for a trialkoxysilyl group. The reaction can be carried out at a temperature ranging from about 0 to about 150° C. and all subranges therebetween while maintaining a pressure in the range of from about 0.1 to about 2000 mm Hg absolute. In one embodiment, the temperature can range from about 30° C. to about 90° C. and all subranges therebetween. In another embodiment, the pressure can range from about 1 to about 80 mm Hg absolute. As those skilled in the art will recognize, excess diol can be utilized to increase reaction rate, but it is not necessary under these conditions as it may increase the cost. The reaction can be carried out by slowly adding diol to the blocked mercaptofunctional alkoxysilane at the desired reaction temperature and vacuum. As the lower boiling mono alcohol is formed, it can be removed from the reaction mixture by a distillation cycle. Removal of the mono alcohol helps drive the reaction to completion. The reactions optionally can be catalyzed using a transesterification catalyst. Suitable tranesterification catalysts are strong protic acids whose pK$_a$ are below 5.0, transition metal complexes such as complexes of tin, iron, titanium and other metal catalysts. Catalysts suitable for these reaction are disclosed in, "The Siloxane Bond, Physical Properties and Chemical Transformations", M. G. Voronkov, V. P. Mileshkevich and Yu. A. Yuzhelevskii, Consultants Bureau, a division of Plenum Publishing Company, New York (1978), Chapter 5 and are included by reference herein. Strong bases are generally unsuitable as transesterification catalysts since they promote the reaction of the blocked mercaptofunctional group with the diol and result in removal of the blocking group. The acid or metal catalysts can be used at a range of about 10 ppm to about 2 weight percent.

After the transesterification reaction has reached completion, a strong base may be added to partially remove blocking groups. In one embodiment, suitable bases are those with a pK$_b$ below 5.0 including, but not limited to, metal alkoxides, amides (—NR$_2$), mercaptides and carbonates wherein the metal ion is lithium, sodium or potassium. The amount of blocking group that is removed is dependent upon the amount of base added. It is understood that the strong base will first neutralize any protic acids that were used in the transesterification reaction of the alkoxysilyl groups. Therefore, additional base in excess of that amount needed to remove the desired amount of blocking group will be required to first complete this neutralization and then remove the blocking group to the desired level. In one embodiment, the amount of additional base added is in a range of from about 0.0005 to about 0.05 molar equivalents to the blocked mercapto group. In another embodiment, about 0.001 to about 0.01 molar equivalents of base are added.

After the blocking group has been partially removed, the final mixture can optionally be buffered. Buffering the mixture will inhibit further removal of blocking groups and will thus add to long-term product stability.

The products of the transesterification of blocked mercaptofunctional silane can comprise a considerable fraction of monomeric material in addition to the formation of dimers and other cyclic and bridged oligomers as illustrated by low viscosity reaction products.

The process for making the organofunctional silane compositions of the invention can optionally employ an inert solvent. The solvent may serve as a diluent, carrier, stabilizer, refluxing aid or heating agent. Generally, any inert solvent that does not enter into the reaction or adversely affect the preparative process can be used. In one embodiment, the solvents are liquid under normal conditions and have a boiling point below about 150° C. Examples of suitable solvents include aromatic, hydrocarbon, ether, aprotic, or chlorinated hydrocarbon solvents such as toluene, xylene, hexane, butane, diethyl ether, dimethylformamide, dimethyl sulfoxide, carbon tetrachloride, methylene chloride, and the like.

In one embodiment of the present invention, the process of transesterifying the alkoxysilane with diol can be conducted continuously. In the case of a continuous operation, the process comprises:

a) reacting, in a thin film reactor, a thin film reaction medium comprising at least one silane of Formula 5, at least one diol and, optionally, transesterification catalyst, to provide blocked mercaptosilane that contains a cyclic and/or bridged dialkoxy group, and by-product mono alcohol;

b) vaporizing by-product mono alcohol from the thin film to drive the reaction;

c) optionally, recovering by-product mono alcohol by condensation;

d) partially removing blocking groups by the addition of base;

e) optionally, removing by-products of the deblocking step;

f) recovering the organofunctional silane reaction product(s); and, g) optionally, neutralizing the reaction medium to improve the storage stability of organofunctional silane product(s) therein.

The molar ratio of diol to blocked mercaptofunctional alkoxy silane used in the continuous thin film process will depend upon the number of alkoxy groups that are desired to be replaced with a diol group. Theoretically, a molar ratio of about 0.5 moles of diol is required per alkoxy-silyl group to be transesterified. For a trialkoxy silane, the stoichiometric equivalent molar ratio is about 1, wherein one diol replaces two alkoxy groups. However, in many cases, only one of the hydroxyl groups of the diol reacts with the alkoxysilyl group. These diols are defined as X in Formulae (10) and (11). The diols, referred to herein as "hydroxyalkoxy", reduce the viscosity and inhibit the gelation of the silane. As one skilled in the art will readily recognize, excess diol can be utilized to increase reaction rates.

The method of forming the film can be any of those known in the art. Typical known devices include but are not limited to, falling film or wiped film evaporators. Minimum film thickness and flow rates will depend on the minimum wetting rate for the film forming surface. Maximum film thickness and flow rates will depend on the flooding point for the film and device. The alcohol is vaporized from the film by heating the film, by reducing pressure over the film, or by a combination of both. In one embodiment, mild heating and reduced pressure are utilized to form the structures of this invention. Optimal temperatures and pressures (partial vacuum) for running this process will depend upon the specific blocked mercaptofunctional silane's alkoxy groups and the diol used in the process. Additionally if an optional inert solvent is used in the process, that choice will affect the optimal temperatures and pressures (partial vacuum) utilized. Examples of such solvents include those listed above.

The by-product alcohol vaporized from the film is removed from the reactive distillation device by a standard partial vacuum-forming device and can be condensed, collected, and recycled as feed to other processes. The silane product is recovered by standard means from the reactive distillation device as a liquid phase. If an inert solvent has been used or if additional purification is necessary, the silane product may be fed to another similar distillation device or distillation column to effect that separation.

The addition of the base should occur after the transesterification reaction between the diol and silane is complete. In one embodiment, this reaction can occur in a separate reaction vessel, so that the base does not neutralize the transesterification catalyst or catalyze the removal of the blocking group. The transesterified intermediate product can be continuous by transferred to a second reaction vessel, e.g., by use of a transfer line and gravity, reduced or elevated pressure, or mechanical pump, to facilitate the process. In the second vessel, the deblocking reaction can occur by the addition of base.

Optionally the transesterified reaction products can be neutralized to improve product storage.

In another embodiment of the present invention, a process for preparing the organofunctional silanes containing both free and blocked mercaptan groups comprises:

a) mixing at least one blocked mercaptofunctional silane of chemical structure:

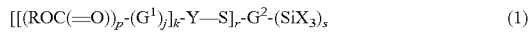
(1)

and/or

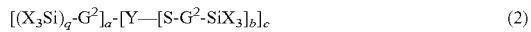
(2)

with a mercaptofunctional silane of chemical formula

(3)

wherein each occurrence of $G^1$, $G^2$, R, Y, X, a, b, c, j, k, p, q, r, and s is as defined above and with the proviso that at least one of X is a hydrolyzable group;

b) reacting the silane mixture from step (a) with a diol $HO(R^0CR^0)_fOH$ wherein f and $R^0$ are as defined above; optionally in the presence of transesterification catalyst;

c) removing by-product mono alcohol; and, d) optionally, neutralizing protonic transesterification catalyst, if utilized, with a base.

The reaction conditions for transesterification of the mixture of free and blocked mercaptofunctional silanes are described above for the blocked mercaptofunctional silane. However, after the transesterification reaction is complete, the reaction mixture can be neutralized if a protic catalyst is used. Neutralization of the catalyst will improve the shelf-stability of the reaction products.

In one embodiment of the present invention, the amount of blocked mercaptofunctional silane of:

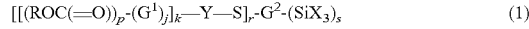
(1)

or

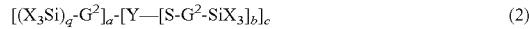
(2)

and the amount of free mercaptofunctional silane of:

(3)

wherein each occurrence of $G^1$, $G^2$, R, Y, X, a, b, c, j, k, p, q, r, and s is as defined above and with the proviso that at least one of the X is a hydrolyzable group, are mixed in a molar ratio of silanes (1) and/or (2) to silane (3) in a range of from about 100:1 to about 0.2:1.

In another embodiment, the molar ratios of silane (1) and/or (2) to silane (3) are in a range of from about 10:1 to about 1:1. If a protic catalyst is used to promote the transesterification of the alkoxysilane with diol, it may be useful to neutralize the catalyst with a base to inhibit the reaction of diol with blocked mercaptan groups. However, only a stoichiometric amount of base is required to neutralize the protic catalyst. Larger amounts of base will promote the removal of blocking group.

In yet another embodiment of the present invention, the process for preparing the organofunctional silane containing both free and blocked mercaptan groups comprises:

a) transesterfying at least one blocked mercaptofunctional silane of:

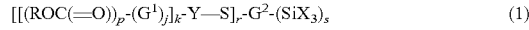
(1)

and/or

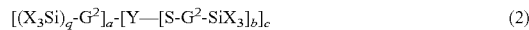
(2)

wherein each occurrence of $G^1$, $G^2$, R, Y, X, a, b, c, j, k, p, q, r, and s is as defined above, and with the proviso that at least one of X is a hydrolyzable group, with at least one diol $HO(R^0CR^0)_fOH$ wherein f and $R^0$ are as defined above, optionally, in the presence of transesterification catalyst;

b) optionally, removing by-product mono alcohol from the reaction mixture resulting from step (a);

c) transesterifying at least one mercaptofunctional silane of:

(3)

wherein each occurrence of $G^2$, X r, and s is as defined above, and with the proviso that at least one of X is a hydrolyzable group, with at least one diol of structure HO(R$^0$CR$^0$)$_f$OH wherein f and R$^0$ are as defined above, optionally, in the presence of transesterification catalyst;

d) optionally, removing by-product mono alcohol from the reaction mixture resulting from step (c);

e) mixing product silane(s) from step (a) with product silane(s) from step (c) to provide a mixture possessing a predetermined amount of mercaptan and blocked mercaptan groups;

f) optionally, neutralizing the product mixture from step (e) with a base if a protic catalyst was utilized.

In one embodiment of the present invention, the molar ratios of the silane prepared in step a and the silane prepared in step d to form silane f are in the range of about 100:1 to about 0.2:1. In another embodiment, the molar ratios of silane from step a and silane from step d to form silane f are in a range from about 10:1 to about 1:1. It is understood that the desired ratio of blocked to free mercapto groups is determine by the mix ratio. The structure of the silane prepared may be bimodal in distribution of the free and blocked mercapto groups. The oligomers and polymers formed may have segments where the nearest neighbors of the free mercapto group are other free mercapto groups and likewise the nearest neighbors of the blocked mercapto group are other blocked mercapto groups. The distribution of free and blocked mercapto groups is therefore not random. The reaction conditions and processes for transesterifying the free and blocked mercaptofunctional silanes are given above.

Further in accordance with the invention, a filled elastomer composition is provided which comprises:

a) at least one elastomer containing carbon-carbon double bonds;

b) at least one inorganic particulate filler; and, c) an organofunctional silane composition comprising at least one organofunctional silane selected from the group consisting of:

(i) mercaptosilane possessing at least one hydroxyalkoxysilyl group and/or a cyclic dialkoxysilyl group, (ii) blocked mercaptosilane possessing at least one hydroxyalkoxysilyl group and/or a cyclic dialkoxysilyl group, (iii) mercaptosilane dimer in which the silicon atoms of the mercaptosilane units are bonded to each other through a bridging dialkoxy group, each silane unit optionally possessing at least one hydroxyalkoxysilyl group or a cyclic dialkoxysilyl group, (iv) blocked mercaptosilane dimer in which the silicon atoms of the blocked mercaptosilane units are bonded to each other through a bridging dialkoxy group, each silane unit optionally possessing at least one hydroxyalkoxysilyl group or a cyclic dialkoxysilyl group, (v) silane dimer possessing a mercaptosilane unit the silicon atom of which is bonded to the silicon atom of a blocked mercaptosilane unit through a bridging dialkoxy group, each silane unit optionally possessing at least one hydroxyalkoxysilyl group or a cyclic dialkoxysilyl group, (vi) mercaptosilane oligomer in which the silicon atoms of adjacent mercaptosilane units are bonded to each other through a bridging dialkoxy group, the terminal mercaptosilane units possessing at least one hydroxyalkoxysilyl group or a cyclic dialkoxysilyl group, (vii) blocked mercaptosilane oligomer in which the silicon atoms of adjacent blocked mercaptosilane units are bonded to each other through a bridging dialkoxy group, the terminal mercaptosilane units possessing at least one hydroxyalkoxysilyl group or a cyclic dialkoxysilyl group, and (viii) silane oligomer possessing at least one mercaptosilane unit and at least one blocked mercaptosilane unit, the silicon atoms of adjacent silane units being bonded to each other through a bridging dialkoxy group, the terminal silane units possessing at least one hydroxyalkoxysilyl group or a cyclic dialkoxysilyl group, with the provisio that, where the composition contains one or more of (i), (iii) and (vi), the composition additionally contains one or more of (ii), (iv), (v), (vii) and (viii), and where the composition contains one or more of (ii), (iv) and (vii), the composition additionally contains one or more of (i), (iii), (v), (vi) and (viii).

In one embodiment of the foregoing filled elastomer composition, the organofunctional silane composition comprises at least one of:

$$[[[(ROC(=O))_p\text{-}(G^1)_j]_k\text{-}Y\text{---}S]_r\text{-}G^2\text{-}(SiX_uZ^b_vZ^c_w)_s]_m$$
$$[(HS)_r\text{-}G^2\text{-}(SiX_uZ^b_vZ^c_w)_s]_n \qquad (10)$$

and/or $$[[(X_uZ^b_vZ^c_wSi)_q\text{-}G^2]_a\text{-}[Y\text{---}[S\text{-}G^2\text{-}SiX_uZ^b_vZ^c_w]_b]_c]_m$$
$$[(HS)_r\text{-}G^2\text{-}(SiX_uZ^b_vZ^c_w)_s]_n \qquad (11)$$

wherein:

each occurrence of Y is independently a polyvalent species $(Q)_zA(=E)$, each wherein an atom (A) attached to an unsaturated heteroatom (E) is attached to a sulfur, which in turn is linked by means of a group $G^2$ to a silicon atom;

each occurrence of R is independently selected from the group consisting of hydrogen, straight, cyclic or branched alkyl that may or may not contain unsaturation, alkenyl groups, aryl groups, and aralkyl groups, wherein each R, other than hydrogen, preferably contains from 1 to 18 carbon atoms;

each occurrence of $G^1$ is independently selected from the group consisting of monovalent and polyvalent groups derived by substitution of alkyl, alkenyl, aryl, or aralkyl wherein $G^1$ contains from 1 to about 30 carbon atoms, with the proviso that if $G^1$ is univalent, $G^1$ can be hydrogen;

each occurrence of $G^2$ is independently selected from the group consisting of monovalent and polyvalent groups derived by substitution of alkyl, alkenyl, aryl, or aralkyl wherein $G^1$ contains from 1 to about 30 carbon atoms;

each occurrence of X is independently selected from the group consisting of —Cl, —Br, RO—, RC(=O)O—, $R_2C$=NO—, $R_2$NO—, $R_2$N—, —R, HO(R$^0$CR$^0$)$_f$O—, wherein each R is as above and each occurrence of R$^0$ is independently given by one of the members listed above for R;

each occurrence of $Z^b$, which forms a bridging structure between two silicon atoms, is independently selected from the group consisting of (—O—)$_{0.5}$, and [—O(R$^0$CR$^0$)$_f$O—]$_{0.5}$, wherein each occurrence of R$^0$ is independently given by one of the members listed above for R;

each occurrence of $Z^c$, which forms a cyclic structure with a silicon atom, is independently given by —O(R$^0$CR$^0$)$_f$O— wherein each occurrence of R$^0$ is independently given by one of the members listed above for R;

each occurrence of Q is independently selected from the group consisting of oxygen, sulfur, and (—NR—);

each occurrence of A is independently selected from the group consisting of carbon, sulfur, phosphorus, and sulfonyl;

each occurrence of E is independently selected from the group consisting of oxygen, sulfur, and (—NR—);

each occurrence of the subscripts, a, b, c, f, j, k, m, n, p, q, r, s, u, v, w, and z is independently given by a is 0 to about 7; b is 1 to about 3; c is 1 to about 6; f is 1 to about 15, j is 0 to about 1, but j may be 0 only if p is 1; k is 1 to 2, with the provisos that if A is carbon, sulfur, or sulfonyl, then (i) a+b=2 and (ii) k=1;

if A is phosphorus, then a+b=3 unless both (i) c>1 and (ii) b=1, in which case a=c+1; and if A is phosphorus, then k is 2;

m is 1 to about 20, n is 1 to about 20, p is 0 to 5, q is 0 to 6; r is 1 to 3; s is 1 to 3; u is 0 to 3; v is 0 to 3; w is 0 to 1 with the proviso that u+v+2w=3; z is 0 to about 3; and with the proviso that the each of the above structures contains at least one hydrolysable group, $Z^b$ or $Z^c$, that is a difunctional alkoxy group.

Also within the scope of the invention are articles of manufacture, particularly tires, made from the foregoing filled elastomer compositions. The invention offers a means for significantly reducing volatile organic compound (VOC) emissions during rubber manufacture and improving the coupling between the organic polymers and inorganic fillers.

The organofunctional silane-based compositions described herein are useful as coupling agents between elastomeric resins (i.e., rubbers) and inorganic fillers. The organofunctional silane compositions are unique in that the high efficiency of the mercaptan group can be utilized without the detrimental side effects typically associated with the use of mercaptosilanes, such as high processing viscosity, less than desirable filler dispersion, premature curing (scorch), and odor. These benefits are obtained because the mercaptan group is part of a high boiling compound that liberates diol or higher polyhydroxy-containing compound upon use. The combination of free and blocked mercapto groups in this silane-based composition allow for a controlled amount of coupling to the organic polymer during the compounding of the rubber. During this non-productive mixing step, the cyclic and/or bridged alkoxysilyl groups may react with the filler and essentially only the free mercaptan groups may react with the rubber. The blocked mercaptan groups remain essentially inactive and are available to help disperse the inorganic filler during the rubber compounding operation. Thus, a controlled amount of coupling of the filler to the polymer occurs during mixing thereby minimizing the undesirable premature curing (scorch) and the associated undesirable increase in viscosity, while promoting the end-use properties such as reinforcing index, which is an indicator of wear. Thus, one can achieve better cured filled rubber properties such as a balance of high modulus and abrasion resistance, resulting from the avoidance or lessening of premature curing.

The organofunctional silane-based compositions herein provide significant advantages over traditional coupling agents that have found extensive use in the rubber and tire industries. These silanes usually contain in their molecular structures three alkoxy groups, e.g., ethoxy groups on each silicon atom, which results in the release of up to three moles of simple monohydroxy alcohol, e.g., ethanol for each silane equivalent during the rubber manufacturing process in which the silane couples to the filler. The release of simple mono alcohols is a great disadvantage because they are it is flammable and therefore pose a threat of fire, and because they contributes so greatly to volatile organic compound (VOC) emissions and are therefore potentially harmful to the environment.

The organofunctional silane-based compositions described herein eliminate or greatly mitigate the foregoing problems by reducing volatile mono alcohol emissions to only one, less than one, and even essentially zero, moles of mono alcohol per silane equivalent. They accomplish this because the silane alkoxy groups are replaced with polyhydroxy alcohols, e.g., diol derived bridging groups, and thus such polyhydroxy alcohols are released during the rubber manufacture process in place of much, or nearly all, of the mono alcohol released. Diols, e.g., having boiling points well in excess of rubber processing temperatures, are not vaporized out of the rubber during the rubber manufacture process, as is the case, e.g., with ethanol, but are retained by the rubber where they migrate to the silica surface due to their high polarity and become hydrogen bonded to the surfaces of siliceous fillers such as silicas. The presence of diols on silica surfaces leads to further advantages not obtainable with ethanol (due to its volatility and ejection during the rubber compounding process) in the subsequent cure process, in which such presence prevents the silica surface from binding the curatives and thereby interfering with the cure. Traditional silanes not based on diols require more curatives to counter losses due to silica binding.

The addition of hydrocarbon-based diols to the rubber compounding formulation prior to and/or concurrent with the addition of curatives is of advantage for the efficient utilization of the curatives, in particular, and polar substances, such as, but not limited to, amines, amides, sulfenamides, thiurams, and guanidines. Whether diols are exclusively added in the form of diol-derived silanes or as free diols in combination with the silane coupling agents, the polarity of the diols is of advantage to the rubber compounding process. These polar substances tend to migrate to the filler surface due to dipole interactions with the filler. This tends to make them unavailable within the organic polymer matrix, where their functions include plasticization of the filled elastomer and acceleration, or retardation, of the curing reactions. The hydrocarbon-based diols enhance the function of the curatives by interfering with their tendency to bind to the silica surface thereby forcing them into the rubber matrix to perform their function. The hydrocarbon-based diols accomplish this by themselves being very polar, and thereby by themselves binding to the filler surface, leaving less room for the curatives to bind to filler. The hydrocarbon-based diols thus act as curative displacing agents from the filler.

The short chain of the hydrocarbon-based diols further enhances their function by a chelate effect. In one embodiment, the number of carbon atoms between the hydroxide groups of $Z^c$ and/or $Z^b$ herein are important and are defined by the divalent radical —O($R^O CR^O)_fO$—, wherein each occurrence of f is 2 or 3. These chains of two or three carbon atoms between the two OH groups of the diol promote the formation of 5- or 6-membered rings when both oxygen atoms bind to a common silicon atom of the silanes of Formulae (10) and (11). This dual binding to a common center, known, and referred to herein as the chelate effect, increases the amount of cyclic dialkoxysilyl group and inhibits the formation of gel. After reactions with the silica in the rubber compounding step, the diols that have been released have a high affinity to the filler because they can chelate with the metal or silicon atom on the filler surface thereby enhancing their ability to prevent the binding of the curatives to the filler.

The hydrocarbon-based diols used herein are superior to ether- and/or polyether-based monofunctional alcohols or difunctional alcohols (diols) because the lack of the ether functionality of the hydrocarbon based diols avoids the problems typically encountered with ethers. These problems include high toxicity, their tendency for spontaneous peroxide formation, and high chain lengths between OH groups. Spontaneous peroxide formation is a problem because it is difficult to prevent and because the peroxides represent flammability hazards. Furthermore, peroxides will decompose when heated to provide free radicals which can initiate unwanted side reactions in the rubber polymers. These side reactions include peroxide-induced cure in which polymer chains are crosslinked. This can lead to premature, excess, and variable crosslinking during or prior to cure. The excess crosslinking can lead to inferior properties in the rubber, premature crosslinking can lead to scorch, and the variability makes it hard to fabricate a reproducible rubber composition and any articles of manufacture derived thereof.

The excess chain lengths of the ether-containing diols forces chelation by the two OH groups to involve ring sizes of at least about 8 atoms, which is well beyond the optimum 5 or 6, accessible to hydrocarbon based diols. Chelation involving an OH group and an ether, which would give the optimum 5 or 6 membered rings, is not as strong as chelation with the two OH groups accessible to the hydrocarbon based diols because the OH groups are less sterically hindered and because the OH groups are more active at forming hydrogen bond interactions, which are key to binding the diols to the filler surface.

An important advantage of the silanes herein is that the by-products of the silane coupling process are themselves of utility in enhancing the rubber compounding process, the value of the resulting rubber compositions, and/or any articles of manufacture employing the rubber compositions. Thus, the blocked mercaptan groups of the silanes of the present invention not only retards coupling of silane to polymer during mixing but also assists in the dispersion of the filler into the polymer during mixing by reducing the ability of the surface hydroxyl or metal oxides to form hydrogen bonds between filler particles, thereby enhancing the ease and completeness of filler dispersion and retarding the reversal of this process, namely, filler reagglomeration. In addition, the diols released from the silane's silicon atoms during the process of coupling to the filler are not just shed as a waste product, but perform an important follow-up function, specifically, enhancing the efficiency of the curatives, as previously described.

An unexpected result of the organofunctional silanes of the present invention is the long scorch times for uncured filled elastomers containing silanes (10) and (11). The high levels of mercapto-functional groups that are present in these silanes would normally produce very short scorch times. Long scorch times are desirable because they allow the uncured rubber to be mixed with the fillers and other ingredients in a single pass and at higher temperatures, which facilitate filler dispersion and uniform composition, without generating high and variable viscosities or partially cured compounds. Uncured filled elastomers with high viscosities are undesirable because they slow down the extrusion rates and fabrication of the articles. If the uncured rubber compound is partially cured before the molding process begins, then the gel particles resulting from premature crosslinking may generate defects and negatively affect one or more of the physical properties of the cured elastomer.

In use, at least one of the organofunctional silane compositions that contain cyclic and/or bridging dialkoxysilyl groups and free and blocked mercapto groups is mixed with the organic polymer before, during, or after the compounding of the filler into the organic polymer. In one embodiment, the silanes are added before or during the compounding of the filler into the organic polymer because these silanes facilitate and improve the dispersion of the filler. The total amount of silane present in the resulting rubber composition should be about 0.05 to about 25 parts by weight per hundred parts by weight of organic polymer (phr). In another embodiment, the amount of silane present in the rubber is from about 1 to 10 phr. Fillers can be used in quantities ranging from about 5 to about 100 phr, more preferably from 25 to 80 phr.

When reaction of the mixture to couple the filler to the polymer is desired, a deblocking agent is added to the mixture to deblock the organofunctional silane compositions that contain cyclic and/or bridging dialkoxysilyl groups and free and blocked mercapto groups. The deblocking agent may be added at quantities ranging from about 0.1 to about 5 phr; more preferably in the range of from about 0.5 to about 3 phr. If alcohol or water are present in the mixture (as is common), a catalyst (e.g., tertiary amines, or Lewis acids) may be used to initiate and promote the loss of the blocking group by hydrolysis or alcoholysis to liberate the corresponding mercaptosilane. Alternatively, the deblocking agent may be a nucleophile containing a hydrogen atom sufficiently labile such that hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group. This transfer of the blocking group from the silane to the nucleophile could be driven, for example, by a greater thermodynamic stability of the products (mercaptosilane and nucleophile containing the blocking group) relative to the initial reactants (organofunctional silane compositions that contain cyclic and/or bridging dialkoxysilyl groups and free and blocked mercapto groups and the nucleophile). For example, if the nucleophile were an amine containing an N—H bond, transfer of the blocking group from the organofunctional silane compositions that contain cyclic and/or bridging dialkoxysilyl groups and free and blocked mercapto groups would yield the mercaptosilane and one of several classes of amides corresponding to the type of blocking group used. For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, and phosphinyl blocking groups deblocked by amines would yield phosphinamides. What is important is that regardless of the blocking group initially present on the cyclic and bridging dialkoxy blocked mercaptofunctional silane and regardless of the deblocking agent used, the initially substantially inactive (from the standpoint of coupling to the organic polymer) organofunctional silane compositions that contain cyclic and/or bridging dialkoxysilyl groups and free and blocked mercapto groups is substantially converted at the desired point in the rubber compounding procedure to the active mercaptosilane. It is noted that partial amounts of the nucleophile may be used (i.e., a stoichiometric deficiency), if one were to only deblock part of the organofunctional silane compositions that contain cyclic and/or bridging dialkoxysilyl groups and free and blocked mercapto groups to control the degree of vulcanization of a specific formulation.

Water typically is present on the inorganic filler as a hydrate or bound to the filler in the form of a hydroxyl group. The deblocking agent can be added in the curative package or, alternatively, at any other stage in the compounding process as a single component. Examples of nucleophiles would include any primary or secondary amines, or amines containing C=N double bonds, such as imines or guanidines; with the proviso that said amine contains at least one N—H (nitrogen-hydrogen) bond. Numerous specific examples of guanidines, amines, and imines well known in the art, which are useful as components in curatives for rubber, are cited in *Rubber Chemicals*; J. Van Alphen; Plastics and Rubber Research Institute TNO, Delft, Holland; 1973. Some examples include: N,N'-diphenylguanidine, N,N',N"-triphenylguanidine, N,N'-di-ortho-tolylguanidine, ortho-biguanide, hexamethylenetetramine, cyclohexylethylamine, dibutylamine, and 4,4'-diaminodiphenylmethane. Any general acid catalysts used to transesterify esters, such as Bronsted or Lewis acids, could be used as catalysts.

The rubber composition need not be, but preferably is, substantially free of functionalized siloxanes, especially those of the type disclosed in Australian Patent AU-A-10082/97, which is incorporated herein by reference. Most preferably, the rubber composition is free of functionalized siloxanes.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients are usually blended in at least one, and often (in the case of silica filled low rolling resistance tires) two, preparatory thermomechanical mixing stage(s) in suitable mixers. Such preparatory mixing is referred to as non-productive mixing or non-productive mixing steps or stages. Such preparatory mixing usually is conducted at temperatures in the range of from about 140° C. to about 200° C. and often in the range of from about 150° C. to about 180° C.

Subsequent to such preparatory mix stages, in a final mixing stage, sometimes referred to as a productive mix stage, deblocking agent (in the case of this invention), curing agents, and possibly one or more additional ingredients, are mixed with the rubber compound or composition, typically at a temperature in a range of 50° C. to 130° C., which is a lower temperature than those utilized in the preparatory mix stages to prevent or retard premature curing of the sulfur curable rubber, which is sometimes referred to as scorching of the rubber composition.

The rubber mixture, sometimes referred to as a rubber compound or composition, typically is allowed to cool, sometimes after or during a process intermediate mill mixing, between the aforesaid various mixing steps, for example, to a temperature of about 50° C. or lower.

When it is desired to mold and to cure the rubber, the rubber is placed into the appropriate mold at about at least 130° C. and up to about 200° C., which will cause the vulcanization of the rubber by the mercapto groups on the mercaptosilane and any other free sulfur sources in the rubber mixture.

By thermomechanical mixing, it is meant that the rubber compound, or composition of rubber and rubber compounding ingredients, is mixed in a rubber mixture under high shear conditions where it autogenously heats up as a result of the mixing, primarily due to shear and associated friction within the rubber mixture in the rubber mixer. Several chemical reactions may occur at various steps in the mixing and curing processes.

The first reaction is a relatively fast reaction and is considered herein to take place between the filler and the alkoxysilane group of the cyclic and/or bridging dialkoxy blocked mercaptofunctional silanes. Such reaction may occur at a relatively low temperature, such as, for example, about 120° C. The second and third reactions are considered herein to be the deblocking of the cyclic and/or bridging dialkoxy blocked mercaptofunctional silanes and the reaction which takes place between the sulfur-containing portion of the silane (after deblocking), and the sulfur vulcanizable rubber at a higher temperature; for example, above about 140° C.

Another sulfur source may be used, for example, in the form of elemental sulfur as $S_8$. A sulfur donor is considered herein as a sulfur-containing compound that liberates free, or elemental sulfur, at a temperature in a range of about 140° C. to about 190° C. Such sulfur donors may be, for example, although are not limited to, polysulfide vulcanization accelerators and organosilane polysulfides with at least two connecting sulfur atoms in their polysulfide bridge. The amount of free sulfur source addition to the mixture can be controlled or manipulated as a matter of choice relatively independently from the addition of the aforesaid cyclic and bridging dialkoxy blocked mercaptofunctional silane composition.

Thus, for example, the independent addition of a sulfur source may be manipulated by the amount of addition thereof and by sequence of addition relative to addition of other ingredients to the rubber mixture.

In an embodiment of the present invention, a rubber composition is prepared by a process comprising the sequential steps of:

(a) thermomechanically mixing, in at least one preparatory mixing step, to a temperature of 140° C. to 200° C., alternatively to 140° C. to 190° C., for a total mixing time of 2 to 20, alternatively 4 to 15, minutes for such mixing step(s):

i) 100 parts by weight of at least one sulfur vulcanizable rubber selected from conjugated diene homopolymers and copolymers, and copolymers of at least one conjugated diene and aromatic vinyl compound, ii) 5 to 100, preferably 25 to 80, phr of particulate filler, wherein the filler preferably contains from 1 to 85 weight percent carbon black, and iii) 0.05 to 20 parts by weight filler of at least one cyclic and/or bridging dialkoxy silane of the present invention composition;

b) subsequently blending therewith, in a final thermomechanical mixing step at a temperature to 50° C. to 130° C. for a time sufficient to blend the rubber, preferably between 1 to 30 minutes, more preferably 1 to 3 minutes, at least one deblocking agent at about 0.05 to 20 parts by weight of the filler and a curing agent at 0 to 5 phr; optionally, and, c) curing said mixture at a temperature in the range of from 130 to 200° C. for about 5 to 60 minutes.

The process may also comprise the additional steps of preparing an assembly of a tire or sulfur vulcanizable rubber with a tread comprised of the rubber composition prepared according to this invention and vulcanizing the assembly at a temperature in a range of 130° C. to 200° C.

Suitable organic polymers and fillers are well known in the art and are described in numerous texts, of which two examples include *The Vanderbilt Rubber Handbook*; R. F. Ohm, ed.; R. T. Vanderbilt Company, Inc., Norwalk, Conn.; 1990 and *Manual For The Rubber Industry*; T. Kempermann, S. Koch, J. Sumner, eds.; Bayer AG, Leverkusen, Germany; 1993. Representative examples of suitable polymers include solution styrene-butadiene rubber (SSBR), styrene-butadiene rubber (SBR), natural rubber (NR), polybutadiene (BR), ethylene-propylene co- and ter-polymers (EP, EPDM), and acrylonitrile-butadiene rubber (NBR).

The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (ESBR) may be used having a relatively conventional styrene content of 20 to 28 percent bound styrene or, for some applications, an ESBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene based rubbers for use in this invention.

The solution polymerization prepared SBR (SSBR) typically has a bound styrene content in a range of 5 to 50, preferably 9 to 36, percent. Polybutadiene elastomer may he conveniently characterized, for example, by having at least a 90 weight percent cis-1,4-content.

Representative examples of suitable filler materials include metal oxides, such as silica (pyrogenic and precipitated), titanium dioxide, aluminosilicate, and alumina, siliceous materials, including clays and talc, and carbon black. Particulate, precipitated silica is also sometimes used for such purpose, particularly in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions is known, see, for example, U.S. Pat. No. 5,116,886 and EP 631 982.

The organofunctional silane compositions that contain cyclic and/or bridging dialkoxysilyl groups and free and blocked mercapto groups may be premixed, or pre-reacted, with the filler particles or added to the rubber mix during the rubber and filler processing, or mixing stage. If the silane and filler are added separately to the rubber mix during the rubber and filler mixing, or processing stage, it is considered that the organofunctional silane compositions that contain cyclic and/or bridging dialkoxysilyl groups and free and blocked mercapto groups then couple in situ to the filler.

The vulcanized rubber composition should contain a sufficient amount of filler to contribute a reasonably high modulus and high resistance to tear. The combined weight of the filler may be as low as about 5 to 100 phr, but is more preferably from 25 to 85 phr.

In one embodiment of the present invention, precipitated silica is utilized as filler. The silica filler herein may as characterized by having a BET surface area, as measured using nitrogen gas, preferably in the range of from about 40 to about 600 $m^2$/g, and more preferably in a range of from about 50 to about 300 $m^2$/g. The BET method of measuring surface area is described in the *Journal of the American Chemical Society*, Volume 60, page 304 (1930). The silica typically may also be characterized by having a dibutylphthalate (DBP) absorption value in a range of from about 100 to about 350, and more usually from about 150 to about 300. Further, useful silica fillers, as well as the aforesaid alumina and aluminosilicate fillers, may be expected to have a CTAB surface area in a range of from abot 100 to about 220 $m^2$/g. The CTAB surface area is the external surface area as evaluated by cetyl trimethylammonium bromide with a pH of 9. The method is described in ASTM D 3849.

Mercury porosity surface area is the specific surface area determined by mercury porosimetry. For such technique, mercury is penetrated into the pores of the sample after a thermal treatment to remove volatiles. Set-up conditions may be suitably described as using a 100 mg sample; removing volatiles during 2 hours at 105° C. and ambient atmospheric pressure; and ambient to 2000 bars pressure measuring range. Such evaluation may be performed according to the method described in Winslow, et al. in ASTM bulletin, p. 39 (1959) or according to DIN 66133. For such an evaluation, a CARLO-ERBA Porosimeter 2000 may be used. The average mercury porosity specific surface area for the selected silica filler should be in a range of 100 to 300 $m^2$/g.

In one embodiment, a suitable pore size distribution for the silica, alumina and aluminosilicate according to such mercury porosity evaluation is considered herein to be: five percent or less of its pores having a diameter of less than about 10 nm; from about 60 to about 90 percent of its pores have a diameter of from about 0 to about 100 nm; from 10 to about 30 percent of its pores having a diameter of from about 100 to about 1,000 nm; and from about 5 to about 20 percent of its pores have a diameter of greater than about 1,000 nm. In a second embodiment, the silica may be expected to have an average ultimate particle size, for example, in the range of from about 0.01 to about 0.05 μm as determined by electron microscopy, although the silica particles may be even smaller, or possibly larger, in size. Various commercially available silicas may be considered for use herein such as, those available from PPG Industries under the HI-SIL trademark, in particular, HI-SIL 210, 243, etc.; silicas available from Rhone-Poulenc, e.g., ZEOSIL 1165 MP; silicas available from Degussa, e.g., VN2 and VN3, etc. and silicas available from Huber, e.g., HUBERSIL 8745.

Where it is desired for the rubber composition, which contains both a siliceous filler such as silica, alumina and/or aluminosilicates and also carbon black reinforcing pigments, to be primarily reinforced with silica as the reinforcing pigment, it is often preferable that the weight ratio of such siliceous fillers to carbon black is at least 3/1 and preferably at least 10/1 and, thus, in a range of 3/1 to 30/1. The filler may comprise from about 15 to about 95 weight percent precipitated silica, alumina and/or aluminosilicate and, correspondingly from about 5 to about 85 weight percent carbon black, wherein the said carbon black has a CTAB value in a range of from about 80 to about 150. Alternatively, the filler may comprise from about 60 to about 95 weight percent of said silica, alumina and/or aluminosilicate and, correspondingly, from about 40 to about 5 weight percent of carbon black. The siliceous filler and carbon black may be pre-blended or blended together in the manufacture of the vulcanized rubber.

The rubber composition can be compounded by methods known in the rubber compounding art, such as mixing the various sulfur-vulcanizable constituent rubbers with various commonly used additive materials as, for example, curing aids such as sulfur, activators, retarders and accelerators, processing additives such as oils, resins e.g., tackifying resins, silicas, plasticizers, fillers, pigments, fatty acid, zinc oxide, waxes, antioxidants and antiozonants, peptizing agents, and reinforcing materials such as, for example, carbon black, and the like. Depending on the intended use of the sulfur vulcanizable and sulfur vulcanized material (rubbers), the additives mentioned above are selected and commonly used in conventional amounts.

The vulcanization can be conducted in the presence of an additional sulfur vulcanizing agent. Examples of suitable sulfur vulcanizing agents include, e.g., elemental sulfur (free sulfur) or sulfur donating vulcanizing agents, for example, an amino disulfide, polymeric polysulfide or sulfur olefin adducts, which are conventionally added in the final, productive, rubber composition mixing step. The sulfur vulcanizing agents (which are common in the art) are used, or added in the productive mixing stage, in an amount ranging from about 0.4 to about 3 phr, or even, in some circumstances, up to about 8 phr, with a range of from about 1.5 to about 2.5 phr, and in some cases from about 2 to about 2.5 phr, being preferred.

Vulcanization accelerators, i.e., additional sulfur donors, may also be used. It will be appreciated that they may be, for example, of the type, such as, for example, benzothiazole, alkyl thiuram disulfide, guanidine derivatives, and thiocarbamates. Representative of such accelerators are, e.g., but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors, include, e.g., thiuram and morpholine derivatives. Representative of such donors include, e.g., but are not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide and disulfidecaprolactam.

Accelerators are used to control the time and/or temperature required for vulcanization and to improve the properties of the vulcanizate. In one embodiment, a single accelerator system can be used, i.e., a primary accelerator. Conventionally and preferably, a primary accelerator(s) is used in total amounts ranging from about 0.5 to about 4, preferably from about 0.8 to about 1.5, phr. Combinations of a primary and a secondary accelerator might be used with the secondary accelerator being used in smaller amounts (e.g., from about 0.05 to about 3 phr) in order to activate and to improve the properties of the vulcanizate. Delayed action accelerators may be used. Vulcanization retarders can also be used. Suitable types of accelerators are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

Typical amounts of tackifier resins, if used, can be from about 0.5 to about 10 phr, usually from about 1 to about 5 phr. Typical amounts of processing aids comprise from about 1 to about 50 phr. Such processing aids can include, e.g., aromatic, naphthenic and/or paraffinic processing oils. Typical amounts of antioxidants are from about 1 to about 5 phr. Representative antioxidants include, e.g., diphenyl-p-phenylenediamine and others, e.g., those disclosed in the Vanderbilt Rubber Handbook (1978), pages 344-346. Typical amounts of antiozonants, are from about 1 to about 5 phr. Typical amounts of fatty acids, if used, which can include stearic acid, are from about 0.5 to about 3 phr. Typical amounts of zinc oxide are from about 2 to about 5 phr. Typical amounts of waxes are from about 1 to about 5 phr. Often microcrystalline waxes are used. Typical amounts of peptizers are from about 0.1 to about 1 phr. Typical peptizers include, e.g., pentachlorothiophenol and dibenzamidodiphenyl disulfide.

The rubber compositions of this invention can be used for various purposes. For example, they can be used for various tire compounds, shoe soles and other industrial goods. Such articles can be built, shaped, molded and cured by various known and conventional methods as is readily apparent to those skilled in the art. One particularly useful application of the rubber compositions herein is for the manufacture of tire treads. An advantage of tires, tire treads, or other articles of manufacture derived from the rubber compositions herein is that they suffer from less VOC emissions during their lifetime and use as a result of having been manufactured from a rubber compound that contains less residual silane ethoxy groups than do rubber compounds of the known and currently practiced art. This is a direct result of having used dialkoxy-functional silane coupling agents in their manufacture, which contain fewer or essentially no ethoxy groups on silicon, relative to the silane coupling agents of the currently known and practiced art. The lack or reduction of ethoxysilane groups in the coupling agents used results in fewer residual ethoxy groups on silicon after the article of manufacture is produced, from which less or no ethanol can be released by hydrolysis of the residual ethoxysilane groups by exposure of the article of manufacture to water during use.

The rubber compositions herein and the articles of manufacture derivable therefrom as described herein are novel in that both contain non-silicon-containing ethoxy esters and esters of hydrocarbon-based diols, as well as the hydrocarbon based diols. Typical examples of such species contained in the rubber compositions and articles of manufacture described herein include octanoate, hexanoate, decanoate, and/or dodecanoate esters of diols such as propanediols, pentane diols, ethylene glycol, and propylene glycol. Additional species would include ethyl octanoate, ethyl hexanoate, ethyl decanoate, and/or ethyl dodecanoate. These species possess polarities intermediate between those of the rubber polymers and the filler, thereby helping to stabilize the compositions and articles of manufacture from filler reagglomeration and the resulting degradation of the properties and performance parameters thereof.

All references cited herein are incorporated herein as they are relevant to the present invention.

The invention may be better understood by reference to the following examples in which the parts and percentages are by weight unless otherwise indicated.

Comparative Examples 1-3

Comparative Examples 1-3 were prepared by mixing 3-thiooctanoylpropyltriethoxysilane and 3-mercaptopropyltriethoxysilane in the ratio indicated in Table 1.

TABLE 1

| Silane | Comparative Example 1 | Comparative Example 2 | Comparative Example 3 |
|---|---|---|---|
| 3-thiooctanoylpropyltriethoxysilane | 100 | 92.7 | 85.4 |
| 1-mercaptopropyltriethoxysilane | 0 | 7.3 | 14.6 |

Example 1

3-Thiooctanoylpropyltriethoxysilane (1101 g; 3.03 moles) was added to a round-bottomed flask. Sulfuric acid (0.98 g) was added to the reaction flask and 2-methylpropane-1,3-diol (816.6 g; 9.06 moles) was added via addition funnel. The flask was heated to 50° C. under a vacuum of 50 torr. Ethanol (367 g) was collected. A 21% ethanolic solution of sodium ethoxide (9.53 g) was added and the mixture was heated to 100-120° C. under atmospheric pressure for several hours.

Example 2

3-thiooctanoylpropyltriethoxysilane (1101 g; 3.03 moles) was added to a round-bottomed flask. Sulfuric acid (0.98 g) was added to the reaction flask and 2-methylpropane-1,3-diol (816.6 g; 9.06 moles) was added via addition funnel. The flask was heated to 50° C. under a vacuum of 50 torr. Ethanol (367 g) was collected. A 21% ethanolic solution of sodium ethoxide (10.7 g) was added and the mixture was heated to 100-120° C. under atmospheric pressure for several hours.

Example 3

3-thiooctanoylpropyltriethoxysilane (1101 g; 3.03 moles) was added to a round-bottomed flask. Sulfuric acid (0.98 g) was added to the reaction flask and 2-methylpropane-1,3-diol (816.6 g; 9.06 moles) was added via addition funnel. The flask was heated to 50° C. under a vacuum of 50 torr. Ethanol (367 g) was collected. A 21% ethanolic solution of sodium ethoxide (11.3 g) was added and the mixture was heated to 100-120° C. under atmospheric pressure for several hours.

Example 4

3-thiooctanoylpropyltriethoxysilane (293.5 g; 0.81 mole) and 3-mercapto propyltriethoxysilane (32.6 g, 0.12 mole) were added to a round-bottomed flask. Sulfuric acid (0.29 g) was added to the reaction flask and 2-methylpropane-1,3-diol (254.6 g; 4.04 moles) was added via addition funnel. The flask was heated to 50° C. under a vacuum of 50 torr. Ethanol (112.7 g) was collected. A 21% ethanolic solution of sodium ethoxide (0.73 g) was added. 439.8 grams of product were recovered.

Example 5

3-thiooctanoylpropyltriethoxysilane (276.6 g; 0.76 moles) and 3-mercaptopropyltriethoxysilane (69.2 g; 0.25 moles) were added to a round-bottomed flask. Sulfuric acid (0.31 g) was added to the reaction flask and 2-methylpropane-1,3-diol (238.5 g; 2.65 moles) was added via addition funnel. The flask was heated to 50° C. under a vacuum of 50 torr. Ethanol (137.9 g) was collected. A 21% ethanolic solution of sodium ethoxide (1.13 g) was added.

Example 6

Component I was prepared by adding 3-thiooctanoylpropyltriethoxysilane (541.1 g; 1.49 moles) to a round-bottomed flask. Sulfuric acid (0.47 g) was added to the reaction flask and 2-methylpropane-1,3-diol (401.4 g; 4.45 moles) was added via addition funnel. The flask was heated to 50° C. under a vacuum of 50 torr. Ethanol (185.9 g) was collected. A 21% ethanolic solution of sodium ethoxide (3.5 g) was added. Component II was prepared by adding 3-mercaptopropyltriethoxysilane (250 g; 0.91 mole) to a round-bottomed flask. Sulfuric acid (0.26 g) was added to the reaction flask and 2-methylpropane-1,3-diol (283 g; 3.14 moles) was added via addition funnel. The flask was heated to 50° C. under a vacuum of 50 torr. Ethanol (126.7 g) was collected. A 21% ethanolic solution of sodium ethoxide (1.24 g) was added. In a round-bottomed flask were combined Component I (145.2 g) and Component II (54.8 g). The mixture was stirred under nitrogen.

Comparative Examples 4-6

Examples 7-12

Cured rubber compositions in the form of plaques (Comparative Examples 4-6 employing the silanes of Comparative Examples 1-3, respectively, and Examples 7-12 employing the silanes of Examples 1-6, respectively) were prepared and their physical and dynamic properties measured.

A typical silica-rubber SBR formulation was used as described below in Table 2. Mixing was carried out in a 1550 ml Krupp intermeshing mixer. The silane loadings were 8.2 phr.

TABLE 2

| PHR | Silica-Silane/Rubber Formulation |
|---|---|
| | Components |
| 103.2 | sSBR (Buna VSL 5525-1) - (Bayer AG) |
| 25 | BR (Budene 1207) - (Goodyear) |
| 80 | silica - Zeosil 1165MP, (Rhodia) |
| 8.2 | Silane from Comparative Examples 1-3 and Examples 1-6 |
| 4.5 | oil - Sundex 8125 (Sun Oil) |
| 2.5 | zinc oxide - Kadox 720C (ZincCorp.) |
| 1.0 | stearic acid - Industrene R (Witco, Crompton) |
| 2.0 | 6 PPD - Flexzone 7P (Uniroyal, Crompton) |
| 1.5 | Wax - Sunproof Improved (Uniroyal, Crompton) |
| | Final Mix Ingredients |
| 1.4 | Rubbermakers Sulfur 104, Harwick |
| 1.7 | CBS - Delac S (Uniroyal, Crompton) |
| 2.0 | DPG - (Uniroyal, Crompton) |

The procedure for preparing a single non-productive mix is presented in Table 3 below:

TABLE 3

One Pass Procedure; Cooling with water @ 25° C., 68% fill factor:

| Step | Procedure |
|---|---|
| 1 | Add polymers, RDM (ram down mix) 60 seconds |
| 2 | Add 50% silica, all silane, oil, RDM 60 seconds |
| 3 | Add remaining 50% silica, wax, RDM 90 seconds |
| 4 | Dust down, RDM 30 seconds |
| 5 | Add remainder of ingredients, RDM 60 seconds |
| 6 | Dust down, RDM to 160-170° C. (in approx. 2 minutes) by increasing rotor speed |
| 7 | Hold at 170° C. (or higher temperature) for 8 minutes by changing speeds on the mixer. |
| 8 | Dump, sheet off roll mill @ 65-70° C. to cool |

The procedure for preparing a single productive mix involved adding sulfur and accelerators (primary and secondary) into a masterbatch prepared as described in Table 3 on a two-roll mill at 65-70° C. After all the silica filler, silane and oil were incorporated into a given mix, the rpm of the rotors was raised so as to achieve the desired silanization temperature. The mix was then held at that temperature for 8 minutes. The mix procedure are shown in Table 3, above.

Curing and testing of the cured rubber compositions in the form of plaques were carried out according to ASTM standards. In addition, small strain dynamic tests were carried out on a Rheometrics Dynamic Analyzer (ARES—Rheometrics Inc.). The specific curing procedure, measurements and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical Properties:

Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$, $\tan \delta_{max}$ were extracted from the non-linear responses of the rubber compounds at small strains. In some cases, steady state values of $\tan \delta$ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz.

The results for the test plaques of Comparative Examples 4-6 and Examples 7-12 are presented in Table 4.

TABLE 4

Physical and Dynamic Properties of Cured Rubber Compositions: of Comparative Examples 4-6 and Examples 7-12

| | Examples | | | | | | | | |
|---|---|---|---|---|---|---|---|---|---|
| | Comp. Ex. 4 | Comp. Ex. 5 | Comp. Ex. 6 | Ex. 7 | Ex. 8 | Ex. 9 | Ex. 10 | Ex. 11 | Ex. 12 |
| Silane used: | Comp. Ex. 1 | Comp. Ex. 2 | Comp. Ex. 3 | Ex. 1 | Ex. 2 | Ex. 3 | Ex. 4 | Ex. 5 | Ex. 6 |
| % SH Titration | | | | 1.43 | 2.41 | 3.09 | 1.03 | 2.24 | 2.31 |
| Mooney Viscosity @ 100° C. | | | | | | | | | |
| ML 1 + 4 | 59 | 62 | 64 | 64.38 | 64.52 | 65.36 | 62 | 64 | 65.22 |
| Mooney Scorch @ 135° C. | | | | | | | | | |
| $M_V$ | 24 | 29 | 31 | 30.16 | 32.40 | 34.49 | 29 | 31.0 | 32.12 |
| MS 1+, $t_3$, minutes | 8.5 | 6.1 | 5.0 | 7.4 | 7.3 | 7.0 | 7.3 | 6.0 | 6.3 |
| MS 1+, $t_{18}$, minutes | 13.2 | 10.0 | 7.5 | 9.48 | 9.13 | 8.25 | 9.4 | 7.5 | 8.05 |
| Oscillating Disc Rheometer @ 149° C., 1° arc, 30 minute timer | | | | | | | | | |
| $M_L$, dNm | 8.3 | 9.5 | 10.3 | 8.92 | 9.42 | 10.16 | 8.6 | 8.8 | 9.57 |
| $M_H$, dNm | 27.7 | 28.2 | 28.5 | 31.20 | 30.36 | 30.18 | 31.2 | 30.4 | 31.38 |
| $t_{s1}$, minutes | 4.6 | 4.3 | 3.5 | 4.68 | 4.54 | 4.25 | 4.3 | 3.5 | 4.04 |
| t90, minutes | 15.4 | 14.2 | 11.1 | 9.69 | 9.39 | 8.76 | 8.7 | 7.3 | 7.98 |
| $M_H$, dNm-$M_L$ | 19.4 | 18.7 | 18.2 | 22.28 | 20.94 | 20.02 | 22.6 | 21.6 | 21.80 |
| Physical Properties, cured t90 @ 149° C. | | | | | | | | | |
| Hardness, Shore A | 54 | 53 | 53 | 58 | 58 | 57 | 58 | 56 | 58 |
| 25% Modulus, MPa | 0.68 | 0.68 | 0.73 | 0.923 | 0.866 | 0.819 | 0.77 | 0.80 | 0.879 |
| 100% Modulus, MPa | 1.53 | 1.65 | 1.76 | 2.42 | 2.29 | 2.15 | 2.10 | 2.20 | 2.35 |
| 300% Modulus, MPa | 7.30 | 8.78 | 9.82 | 13.32 | 13.98 | 14.20 | 12.02 | 13.36 | 14.03 |
| Tensile, MPa | 22.2 | 22.6 | 23.1 | 21.78 | 20.36 | 19.03 | 22.0 | 21.7 | 19.98 |
| RI 300/25 | 10.74 | 12.91 | 13.45 | 14.43 | 16.14 | 17.34 | 15.6 | 16.7 | 15.96 |
| RI 300/100 | 4.78 | 5.32 | 5.58 | 5.50 | 6.10 | 6.60 | 5.7 | 6.1 | 5.97 |
| Dynamic Properties in the Cured State | | | | | | | | | |
| Non-linearity (0-10%) @ 60° C. | | | | | | | | | |
| G', initial, MPa | | | | 2.51 | 2.67 | 2.23 | 2.15 | 2.02 | 2.87 |
| Delta G', MPa | | | | 1.06 | 1.19 | 0.84 | 0.79 | 0.69 | 1.35 |
| $G''_{max}$, MPA | | | | 0.29 | 0.33 | 0.25 | 0.233 | 0.205 | 0.32 |
| $\tan \delta_{max}$ | | | | 0.14 | 0.14 | 0.13 | 0.126 | 0.121 | 0.14 |
| Low Temperature Viscoelasticity | | | | | | | | | |
| tan delta, 0° C. | | | | 0.54 | 0.55 | 0.54 | 0.568 | 0.560 | 0.55 |
| tan delta, 60° C. | | | | 0.13 | 0.13 | 0.12 | 0.119 | 0.113 | 0.12 |
| G', 0° C., MPa | | | | 5.50 | 5.42 | 4.65 | 5.20 | 4.77 | 5.54 |
| G', 60° C., MPa | | | | 1.92 | 1.92 | 1.72 | 1.72 | 1.69 | 1.96 |

As shown by the data presented in Table 4, the organofunctional and cyclic and/or bridging dialkoxy silane compositions of the present invention (Examples 1-6) show equivalent or improved performance while maintaining the long scorch times necessary for mixing, extrusion and fabricating articles. These silane compositions also offer a significant benefit in reducing the amounts of VOCs that are released.

Comparative Examples 7 and 8

During the compounding of rubber, 3-thiooctanoylpropyltriethoxysilane (6.64 phr), 3-mercaptopropyltriethoxysilane (1.56 phr), and 2-methyl-1,3-propanediol (2.0 phr) were added, as described in the mixing procedure of Table 3, to provide the test plaque of Comparative Example 8. The uncured filled elastomer of Comparative Example 7, exhibited very short scorch times, as shown in Table 5, infra.

Example 13

Thiooctanoylpropyltriethoxysilane (213 g) was added to a round-bottomed flask. Sulfuric acid (0.25 g) and trimethylolpropane (235 g) were added to the reaction flask. The flask was heated to 70° C. under a vacuum of 50 torr. The trimethylolpropane melted and dissolved. Ethanol (80 g) was collected. A 21% ethanolic solution of sodium ethoxide (0.97 g) was added and the mixture was heated to 100-120° C. under atmospheric pressure for several hours.

Example 14

To a 2-liter round bottomed flask was charged 3-octanoylthio-1-propyltriethoxysilane (602 grams; 1.65 moles) and diethylene glycol (526 grams; 4.96 moles). A catalytic amount (0.8 grams) of para-toluenesulfonic acid (PTSA) was then added to the mixture. The 2-liter flask with its contents was then immediately placed onto a rotary evaporator. The contents were subject to rotary evaporation using a mechanical pump as a vacuum source, a dry ice trap as a condenser, a needle valve as a flow regulator between the dry ice trap and vacuum pump, and a heated water bath as a dual source of heat and buoyancy. Rotary evaporation was begun with the water bath at ambient temperature, which was gradually raised to and then maintained at a maximum of 70° C. Rotary evaporation was continued until no more condensation of ethanol was evident in the dry ice trap. The total time of rotary evaporation was 3.5 hours. The quantity of ethanol collected in the trap (213 grams; 4.63 moles) is consistent with 93% transesterification of the triethoxysilane group on the starting silane to DEG functionality. This reactant product is designated Silane A.

To a 2-liter round bottomed flask was charged 3-mercapto-1-propyltriethoxysilane (238 grams; 1.00 mole) and diethylene glycol (318.4 grams; 3.00 moles). A catalytic around (0.5 grams) of para-toluenesulfonic acid (PTSA) was then added to the mixture. The 2-liter flask with its contents was then immediately placed onto a rotary evaporator. The contents were subject to rotary evaporation using a mechanical pump as a vacuum source, a dry ice trap as a condenser, a needle valve as a flow regulator between the dry ice trap and vacuum pump, and a heated water bath as a dual source of heat and buoyancy. Rotary evaporation was begun with the water bath at ambient temperature, which was gradually raised to and then maintained at a maximum of 64° C. Rotary evaporation was continued until no more condensation of ethanol was evident in the dry ice trap. The quantity of ethanol collected in the trap (133 grams; 2.9 moles) is consistent with 97% transesterification of the triethoxysilane group on the starting silane to DEG functionality. This reaction product is designated Silane B.

Into a 100 ml round bottom flask equipped with a mechanical stirrer was charged Silane A (85 grams). Silane A was stirred at room temperature and then slowly Silane B (15 grams) was added thereto. This mixture of Silane A and B is designated Silane C.

Example 15

Into a 100 ml round bottom flask equipped with a mechanical stirrer was charged Silane A (65 grams). Silane A was stirred at room temperature and then slowly Silane B (35 grams) was added. The mixture of Silane A and B is designated Silane D.

Example 16

To a 2-liter round bottomed flask was charged 3-octanoylthio-1-propyltriethoxysilane (234 grams; 0.64 moles), 3-mercapto-1-propyltriethoxysilane (76.7 grams; 0.32 moles), and diethylene glycol (307 grams; 2.89 moles). A catalytic amount (0.4 grams) of para-toluenesulfonic acid (PTSA) was then added to the mixture. The 2-liter flask with its contents was then immediately placed onto a rotary evaporator. The contents were subject to rotary evaporation using a mechanical pump as a vacuum source, a dry ice trap as a condenser, a needle valve as a flow regulator between the dry ice trap and vacuum pump, and a heated water bath as a dual source of heat and buoyancy. Rotary evaporation was begun with the water bath at ambient temperature, which was gradually raised to and then maintained at a maximum of 96° C. Rotary evaporation was continued until no more condensation of ethanol was evident in the dry ice trap. The total time of rotary evaporation was 4 hours and 30 minutes. The quantity of ethanol collected in the trap (129 grams; 2.8 moles) is consistent with 97% transesterification of the triethoxysilane group on the starting silane to DEG functionality. This reaction product is designated Silane E.

Table 5 below sets forth the properties of the cured rubber test plaques of Comparative Example 8 and examples 17-19.

TABLE 5: Physical and Dynamic Properties of Cured Rubber Compositions of Comparative Example 8 and Examples 17-19:

TABLE 5

|  | Comp. Ex. 8 | Ex. 17 | Ex. 18 | Ex. 19 |
|---|---|---|---|---|
| Silane | Comp. Ex. 7 | Ex. 14 | Ex. 15 | Ex. 16 |
| % SH Titration | 2.5 |  |  |  |
| Mooney Viscosity @ 100° C. |  |  |  |  |
| ML 1 + 4 | 70.9 | 51.8 | 55.0 | 54.1 |
| Mooney Scorch @ 135° C. |  |  |  |  |
| $M_V$ | 44.97 | 24.72 | 26.67 | 26.67 |
| MS 1+, $t_3$, minutes | 0.05 | 5.36 | 4.26 | 5.18 |
| MS 1+, $t_{18}$, minutes | 10.25 | 7.43 | 6.10 | 7.25 |
| Oscillating Disc Rheometer |  |  |  |  |
| @ 149° C., 1° arc, |  |  |  |  |
| 30 minute timer |  |  |  |  |
| $M_L$, dNm | 8.42 | 7.57 | 8.82 | 8.34 |
| $M_H$, dNm | 30.63 | 30.38 | 30.66 | 30.69 |
| $t_{s1}$, minutes | 4.28 | 3.44 | 2.68 | 3.45 |
| t90, minutes | 13.21 | 7.79 | 6.60 | 8.21 |
| $M_H$, dNm-$M_L$ | 22.20 | 22.81 | 21.84 | 22.35 |

TABLE 5-continued

|  | Comp. Ex. 8 | Ex. 17 | Ex. 18 | Ex. 19 |
|---|---|---|---|---|
| Physical Properties, cured t90 @ 149° C. | | | | |
| Hardness, Shore A | 53 | | | |
| Elongation, % | 351 | | | |
| 25% Modulus, MPa | 0.96 | | | |
| 100% Modulus, MPa | 2.54 | | | |
| 300% Modulus, MPa | 15.86 | | | |
| Tensile, MPa | 20.00 | | | |
| RI 300/25 | 16.45 | | | |
| RI 300/100 | 6.25 | | | |

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A process for making an organofunctional silane composition possessing mercaptan functionality and blocked mercaptan functionality which comprises:
    a) reacting at least one silane reactant possessing mercaptan functionality or blocked mercaptan functionality and further possessing at least one transesterifiable group with at least one polyhydroxy-containing compound under transesterification conditions to provide said organofunctional silane composition; and, optionally,
    b) treating part or all of the organofunctional silane composition resulting from step (a) to convert part of the blocked mercaptan functionality, if present therein, to mercaptan functionality, or to convert part of the mercaptan functionality, if present therein, to blocked mercaptan functionality,
    the organofunctional silane composition resulting from step (a) and/or step (b) containing at least one organofunctional silane selected from the group consisting of:
    (i) mercaptosilane possessing at least one hydroxyalkoxysilyl group and/or a cyclic dialkoxysilyl group,
    (ii) blocked mercaptosilane possessing at least one hydroxyalkoxysilyl group and/or a cyclic dialkoxysilyl group,
    (iii) mercaptosilane dimer in which the silicon atoms of the mercaptosilane units are bonded to each other through a bridging dialkoxy group, each silane unit optionally possessing at least one hydroxyalkoxysilyl group or a cyclic dialkoxysilyl group,
    (iv) blocked mercaptosilane dimer in which the silicon atoms of the blocked mercaptosilane units are bonded to each other through a bridging dialkoxy group, each silane unit optionally possessing at least one hydroxyalkoxysilyl group or a cyclic dialkoxysilyl group,
    (v) silane dimer possessing a mercaptosilane unit the silicon atom of which is bonded to the silicon atom of a blocked mercaptosilane unit through a bridging dialkoxy group, each silane unit optionally possessing at least one hydroxyalkoxysilyl group or a cyclic dialkoxysilyl group,
    (vi) mercaptosilane oligomer in which the silicon atoms of adjacent mercaptosilane units are bonded to each other through a bridging dialkoxy group, the terminal mercaptosilane units possessing at least one hydroxyalkoxysilyl group or a cyclic dialkoxysilyl group,
    (vii) blocked mercaptosilane oligomer in which the silicon atoms of adjacent blocked mercaptosilane units are bonded to each other through a bridging dialkoxy group, the terminal mercaptosilane units possessing at least one hydroxyalkoxysilyl group or a cyclic dialkoxysilyl group, and
    (viii) silane oligomer possessing at least one mercaptosilane unit and at least one blocked mercaptosilane unit, the silicon atoms of adjacent silane units being bonded to each other through a bridging dialkoxy group, the terminal silane units possessing at least one hydroxyalkoxysilyl group or a cyclic dialkoxysilyl group, with the provisio that,
    where the organofunctional silane composition resulting from step (a) contains one or more of (i), (iii) and (vi), said composition is combined with one or more of (ii), (iv), (v), (vii) and (viii), and where the organofunctional silane composition resulting from step (a) contains one or more of (ii), (iv) and (vii), said composition is combined with one or more of (i), (iii), (v), (vi) and (viii).

2. The process of claim 1 wherein the silane reactant possesses 1 to 3 transesterifiable alkoxy groups and the transesterifying polyhydroxy-containing compound is a diol.

3. The process of claim 1 wherein the silane reactant possesses 2 or 3 transesterifiable groups and the transesterifying polyhydroxy-containing compound is a diol.

4. The process of claim 2 wherein all of the silane reactant possesses mercaptan functionality.

5. The process of claim 2 wherein all of the silane reactant possesses blocked mercaptan functionality.

6. The process of claim 3 wherein all of the silane reactant possesses mercaptan functionality.

7. The process of claim 3 wherein all of the silane reactant possesses blocked mercaptan functionality.

8. The process of claim 2 wherein one portion of the silane reactant contains mercaptan functionality and the other portion of the silane reactant contains blocked mercaptan functionality.

9. The process of claim 3 wherein one portion of the silane reactant contains mercaptan functionality and the other portion of the silane reactant contains blocked mercaptan functionality.

10. The process of claim 1 wherein step (a) is carried out employing a silane possessing mercaptan functionality exclusively to provide at least one of organofunctional silanes (i), (iii) and (vi), step (a) is also carried out employing a silane possessing blocked mercaptan functionality exclusively to provide at least one of organofunctional silanes (ii), (iv) and (vii) and thereafter at least one of organofunctional silanes (i), (iii) and (vi) is combined with at least one of organofunctional silanes (ii), (iv) and (vii) to provide an organosilane composition containing both mercaptan and blocked mercaptan functionalities.

11. The process of claim 1 wherein the hydroxy-containing compound is at least one member selected from the group consisting of glycerol, trimethylolethane, trimethylolpropane, 1,2,4-butanetriol, 1,2,6-hexanetriol, pentaerythritol, dipentaerythritol, tripentaerythritol, mannitol, galacticol and sorbitol.

12. A process for the preparation of an organofunctional silane comprising:
a) reacting at least one organofunctional silane selected from the group consisting of:

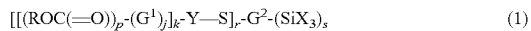  (1)

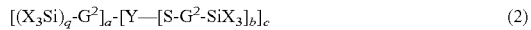  (2)

  (3)

each occurrence of Y is independently selected from a polyvalent species $(Q)_zA(=E)$, wherein the atom (A) attached to an unsaturated heteroatom (E) is attached to a sulfur, which in turn is linked by means of a group $G^2$ to a silicon atom;
  each occurrence of R is independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms;
  each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms, with the proviso that if $G^1$ is univalent, $G^1$ can be hydrogen;
  each occurrence of $G^2$ is independently selected from the group consisting of divalent or polyvalent group derived by substitution of alkyl, alkenyl, aryl, or aralkyl wherein $G^2$ can have from 1 to 30 carbon atoms;
  each occurrence of X is independently selected from the group consisting of —Cl, —Br, RO—, RC(=O)O—, $R_2C=NO$—, $R_2NO$—, $R_2N$—, —R, wherein each R is as above;
  each occurrence of Q is independently selected from the group consisting of oxygen, sulfur, and (—NR—);
  each occurrence of A is independently selected from the group consisting of carbon, sulfur, phosphorus, and sulfonyl;
  each occurrence of E is independently selected from the group consisting of oxygen, sulfur, and (—NR—);
  each occurrence of the subscripts, a, b, c, j, k, p, q, r, s, and z are independently given by a is 0 to about 7; b is 1 to about 3; c is 1 to about 6; j is 0 to about 1, but j may be 0 only if p is 1; k is 1 to 2, with the provisos that
  if A is carbon, sulfur, or sulfonyl, then (i) a+b=2 and (ii) k=1;
  if A is phosphorus, then a+b=3 unless both (i) c>1 and (ii) b=1, in which case a=c+1; and if A is phosphorus, then k is 2; p is 0 to 5, q is 0 to 6; r is 1 to 3; s is 1 to 3; z is 0 to about 3 and with the proviso that each of the above structures contains at least one hydrolysable X group;
b) with at least one polyhydroxy-containing compound of the general formula (6):

  (6)

wherein each occurrence of $G^3$ is a hydrocarbon group of from about 1 to 15 carbon atoms or a heterocarbon group of from about 4 to about 15 carbon atoms containing one or more etheric oxygen atoms and d is an integer of from about 2 to 8, under transesterification reaction conditions, part or all of the product(s) of the reaction being optionally treated to convert blocked mercaptan functionality, if present, to mercaptan functionality, or to convert mercaptan functionality, if present, to blocked mercaptan functionality.

13. The process of claim 12 further comprising:
a) reacting, in a thin film reactor, a thin film reaction medium comprising at least one silane of general formula:

  (4)

  (5)

wherein each R independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms; $G^2$ is an alkylene group of from 1 to about 12 carbon atoms; and, $G^1$ is an alkyl group of from 3 to about 12 carbon atoms, at least one diol and, optionally, transesterification catalyst, to provide blocked mercaptosilane that contains a cyclic and/or bridged dialkoxy group, and by-product mono alcohol;
b) vaporizing by-product mono alcohol from the thin film to drive the reaction;
c) optionally, recovering by-product mono alcohol by condensation;
d) partially removing blocking groups by the addition of base;
e) optionally, removing by-products of the deblocking step;
f) recovering the organofunctional silane reaction product(s); and,
g) optionally, neutralizing the reaction medium to improve the storage stability of organofunctional silane product(s) therein.

14. A process for the preparation of an organofunctional silane comprising:
a) mixing at least one blocked mercaptofunctional silane selected from the group consisting of:

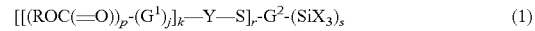  (1)

and

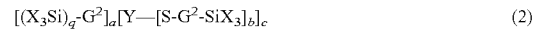  (2)

with a mercaptofunctional silane of chemical formula

  (3)

wherein each occurrence of Y is independently selected from a polyvalent species $(Q)_zA(=E)$, wherein the atom (A) attached to an unsaturated heteroatom (E) is attached to a sulfur, which in turn is linked by means of a group $G^2$ to a silicon atom;
  each occurrence of R is independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms;
  each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms, with the proviso that if $G^1$ is univalent, $G^1$ can be hydrogen;
  each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of X is independently selected from the group consisting of —Cl, —Br, RO—, RC(=O)O—, $R_2C=NO$—, $R_2NO$—, $R_2N$—, —R, wherein each R is as above;

each occurrence of Q is independently selected from the group consisting of oxygen, sulfur, and (—NR—);

each occurrence of A is independently selected from the group consisting of carbon, sulfur, phosphorus, and sulfonyl;

each occurrence of E is independently selected from the group consisting of oxygen, sulfur, and (—NR—);

each occurrence of the subscripts, a, b, c, j, k, p, q, r, s, and z are independently given by a is 0 to about 7; b is 1 to about 3; c is 1 to about 6; j is 0 to about 1, but j may be 0 only if p is 1; k is 1 to 2, with the provisos that if A is carbon, sulfur, or sulfonyl, then (i) a+b=2 and (ii) k=1;

if A is phosphorus, then a+b=3 unless both (i) c>1 and (ii) b=1, in which case a=c+1; and if A is phosphorus, then k is 2; p is 0 to 5, q is 0 to 6; r is 1 to 3; s is 1 to 3; z is 0 to about 3 and with the proviso that each of the above structures contains at least one hydrolysable X group;

b) reacting the silane mixture from step (a) with a diol $HO(R^0CR^0)_fOH$ wherein $R^0$ is independently given by one of the members listed above for R, and f is 2 to about 15, optionally in the presence of transesterification catalyst;

c) removing by-product mono alcohol; and, d) optionally, neutralizing protonic transesterification catalyst, if utilized, with a base.

15. The process of claim 14 where the reaction temperature is from about 0° C. to about 150° C.

16. The process of claim 14 where the reaction temperature is from about 30 to about 90° C.

17. The process of claim 14 where the reaction temperature is from about 0.1 to about 2000 mm Hg absolute pressure.

18. The process of claim 14 where the reaction pressure is from about 1 to about 80 mm Hg absolute pressure.

19. The process of claim 14 wherein a molar ratio of at from about 0.1 moles to about 3.0 moles of diol per alkoxysilyl in the silane is employed.

20. The process of claim 14 wherein a molar ratio of from about 0.1 to about 2.5 moles of diol for a trialkoxy silane is employed.

21. The process of claim 14 carried out in the presence of an inert solvent.

22. The process of claim 21 wherein the inert solvent is selected from the group consisting of toluene, xylene, hexane, butane, diethyl ether, dimethyl formamide, dimethyl sulfoxide, carbon tetrachloride, methylene chloride, and mixtures thereof.

23. The process of claim 14 where the film is formed in a falling film evaporator device.

24. The process of claim 23 where the film is formed in a wiped film evaporator device.

25. The process of claim 24 where the film is formed in a distillation column.

26. A process for preparing organofunctional silane comprising:

a) reacting at least one mercaptofunctional silane of selected from the group consisting of:

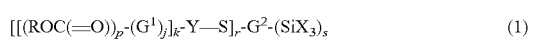 (1)

and

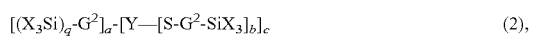 (2), wherein each occurrence of Y is independently selected from a polyvalent species $(Q)_zA(=E)$, wherein the atom (A) attached to an unsaturated heteroatom (E) is attached to a sulfur, which in turn is linked by means of a group $G^2$ to a silicon atom;

each occurrence of R is independently selected from the group consisting of hydrogen, straight, cyclic or branched alkyl that may or may not contain unsaturation, alkenyl groups, aryl groups, and aralkyl groups, wherein each R, other than hydrogen, contains from 1 to 18 carbon atoms;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms, with the proviso that if $G^1$ is univalent, $G^1$ can be hydrogen;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of X is independently selected from the group consisting of —Cl, —Br, RO—, RC(=O)O—, $R_2C=NO$—, $R_2NO$—, $R_2N$—, —R, wherein each R is as above;

each occurrence of Q is independently selected from the group consisting of oxygen, sulfur, and (—NR—);

each occurrence of A is independently selected from the group consisting of carbon, sulfur, phosphorus, and sulfonyl;

each occurrence of E is independently selected from the group consisting of oxygen, sulfur, and (—NR—);

each occurrence of the subscripts, a, b, c, j, k, p, q, r, s, and z are independently given by a is 0 to about 7; b is 1 to about 3; c is 1 to about 6; j is 0 to about 1, but j may be 0 only if p is 1; k is 1 to 2, with the provisos that if A is carbon, sulfur, or sulfonyl, then (i) a+b=2 and (ii) k=1;

if A is phosphorus, then a+b=3 unless both (i) c>1 and (ii) b=1, in which case a=c+1; and if A is phosphorus, then k is 2; p is 0 to 5, q is 0 to 6; r is 1 to 3; s is 1 to 3; z is 0 to about 3 and with the proviso that each of the above structures contains at least one hydrolysable X group, with at least one diol $HO(R^0CR^0)_fOH$ wherein $R^0$ is independently given by one of the members listed above for R, and f is 2 to about 15, optionally, in the presence of transesterification catalyst;

b) optionally, removing by-product mono alcohol from the reaction mixture resulting from step (a);

c) transesterifying at least one mercaptofunctional silane of:

$$(HS)_r\text{-}G^2\text{-}(SiX_3)_s \quad (3)$$

wherein each occurrence of $G^2$, X r, and s is as defined above, and with the proviso that at least one of X is a hydrolyzable group, with at least one diol of structure $HO(R^0CR^0)_fOH$ wherein f and $R^0$ are as defined above, optionally, in the presence of transesterification catalyst;

d) optionally, removing by-product mono alcohol from the reaction mixture resulting from step (c);

e) mixing product silane(s) from step (a) with product silane(s) from step (c) to provide a mixture possessing a predetermined amount of mercaptan and blocked mercaptan groups;

f) optionally, neutralizing the product mixture from step (e) with a base if a protic catalyst was utilized.

27. The process of claim 1 wherein the organofunctional silane is at least one member selected from the group consisting of thioacetic acid 2-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-ethyl ester; thioacetic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; thiobutyric acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid S-[3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl)-propyl]ester; octanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; undecanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; heptanethioic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; heptanethioic acid S-[3-(2-{3-[(3-hydroxy-2-methyl-propoxy)-(3-mercapto-propyl)-methyl-silanyloxy]-2-methyl-propoxy}-5-methyl-[1,3,2]dioxasilepan-2-yl)-propyl]ester; thiopropionic acid 3-{2-[3-((3-mercapto-propyl)-methyl-{2-methyl-3-[5-methyl-2-(3-propionylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester; octanethioic acid 3-{2-[3-((3-mercapto-propyl)-methyl-{2-methyl-3-[5-methyl-2-(3-octanoylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-methyl-(3-octanoylsulfanyl-propyl)-silanyloxy]-2-methyl-propoxy}-methyl-silanyl)-propyl] ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-(3-mercapto-propyl)-methyl-silanyloxy]-2-methyl-propoxy}-methyl-silanyl)-propyl]ester; octanethioic acid S-[3-((3-hydroxy-2-methyl-propoxy)-{3-[{3-[bis-(3-hydroxy-2-methyl-propoxy)-(3-mercapto-propyl)-silanyloxy]-2-methyl-propoxy}-(3-mercapto-propyl)-(3-hydroxy-2-methyl-propoxy)-silanyloxy]-2-methyl-propoxy}-(3-hydroxy-2-methyl-propoxy)-silanyl)-propyl]ester; dimethyl-thiocarbamic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; dimethyl-dithiocarbamic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; dimethyl-dithiocarbamic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; thiocarbonic acid O-ethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; trithiocarbonic acid ethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; trithiocarbonic acid ethyl ester 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; dithiobutyric acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; dithiobutyric acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; diethyl-dithiocarbamic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; diethyl-dithiocarbamic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; N-methyl-thiobutyrimidic acid 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester; N-methyl-thiobutyrimidic acid 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; thiophosphoric acid O,O'-diethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; thiophosphoric acid O-ethyl ester S-[3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl]ester O'-propyl ester; dithiophosphoric acid O-ethyl ester S-[3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl]ester O'-propyl ester; trithiophosphoric acid S,S'-diethyl ester S"-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl] ester; tetrathiophosphoric acid diethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; tetrathiophosphoric acid diethyl ester 3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl ester; tetrathiophosphoric acid ethyl ester 3-((3-hydroxy-2-methyl-propoxy)-{3-[2-(3-mercapto-propyl)-5-methyl-[1,3,2]dioxasilinan-2-yloxy]-2-methyl-propoxy}-methyl-silanyl)-propyl ester propyl ester; methyl-phosphonodithioic acid S-ethyl ester S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; and, dimethyl-phosphinothioic acid S-[3-((3-hydroxy-2-methyl-propoxy)-{3-[(3-hydroxy-2methyl-propoxy)-(3-mercapto-propyl)-methyl-silanyloxy]-2-methyl-propoxy}-methyl-silanyl)-propyl]ester, and mixtures thereof.

28. The process of claim 1 wherein the organofunctional silane is at least one member selected from the group consisting of octanethioic acid S-[3-((3-hydroxy-2-methyl-propoxy)-{3-[{3-[bis-(3-hydroxy-2-methyl-propoxy)-(3-mercapto-propyl)-silanyloxy]-2-methyl-propoxy}-(3-mercapto-propyl)-(3-hydroxy-2-methyl-propoxy)-silanyloxy]-2-methyl-propoxy}-(3-hydroxy-2-methyl-propoxy)-silanyl)-propyl]ester; octanethioic acid S-[3-((3-hydroxy-2-methyl-propoxy)-{3-[{3-[(3-hydroxy-2-methyl-propoxy)-(3-mercapto-propyl)-methyl-silanyloxy]-2-methyl-propoxy}-(3-mercapto-propyl)-methyl-silanyloxy]-2-methyl-propoxy}-methyl-silanyl)-propyl]ester; octanethioic acid 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propyl ester; octanethioic acid S-[3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl)-propyl]ester; octanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl] ester; undecanethioic acid S-[3-(2-{3-[2-(3-mercapto-propyl)-4-methyl-[1,3,2]dioxasilinan-2-yloxy]-butoxy}-4-methyl-[1,3,2]dioxasilinan-2-yl)-propyl]ester; heptanethioic acid S-[3-((3-hydroxy-2-methyl-propoxy)-{3-[(3-hydroxy-2-methyl-propoxy)-(3-mercapto-propyl)-methyl-silanyloxy]-2-methyl-propoxy}-methyl-silanyl)-propyl]ester; heptanethioic acid S-[3-(2-{3-[(3-hydroxy-2-methyl-propoxy)-(3-mercapto-propyl)-methyl-silanyloxy]-2-methyl-propoxy}-5-methyl-[1,3,2]dioxasilepan-2-yl)-propyl]ester; thiopropionic acid 3-{2-[3-((3-mercapto-propyl)-methyl-{2-methyl-3-[5-methyl-2-(3-propionylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester; and octanethioic acid 3-{2-[3-((3-mercapto-propyl)-methyl-{2-methyl-3-[5-methyl-2-(3-octanoylsulfanyl-propyl)-[1,3,2]dioxasilinan-2-yloxy]-propoxy}-silanyloxy)-2-methyl-propoxy]-5-methyl-[1,3,2]dioxasilepan-2-yl}-propyl ester and mixtures thereof.

29. An organofunctional silane composition resulting from the process of claim 1.

30. An organofunctional silane composition resulting from the process of claim 2.

31. An organofunctional silane composition resulting from the process of claim 8.

32. An organofunctional silane composition resulting from the process of claim 9.

33. An organofunctional silane composition resulting from the process of claim 10.

34. An organofunctional silane composition resulting from the process of claim 12.

35. An organofunctional silane composition resulting from the process of claim 13.

36. An organofunctional silane composition resulting from the process of claim 14.

37. An organofunctional silane composition resulting from the process of claim 25.

38. An organofunctional silane composition resulting from the process of claim 26.

\* \* \* \* \*